United States Patent [19]
Varney et al.

[11] Patent Number: 5,945,427
[45] Date of Patent: Aug. 31, 1999

[54] ANTIPROLIFERATIVE SUBSTITUTED 5-THIAPYRIMIDINONE AND 5-SELENOPYRIMIDINONE COMPOUNDS

[75] Inventors: Michael D. Varney, Carlsbad; William H. Romines, San Diego; Cynthia L. Palmer, La Mesa; Judith G. Deal, Temecula, all of Calif.

[73] Assignee: Agouron Pharmaceuticals, Inc., La Jolla, Calif.

[21] Appl. No.: 09/003,163

[22] Filed: Jan. 6, 1998

Related U.S. Application Data

[62] Division of application No. 08/448,556, Jun. 7, 1995, Pat. No. 5,739,141, which is a continuation-in-part of application No. 07/991,259, filed as application No. PCT/US93/11795, Dec. 10, 1993, abandoned.

[51] Int. Cl.$^6$ .................. A61K 31/505; C07D 239/36; C07D 239/48
[52] U.S. Cl. .................. 514/272; 544/320; 544/321
[58] Field of Search .................. 544/320, 321; 514/272

[56] References Cited

U.S. PATENT DOCUMENTS

| | | | |
|---|---|---|---|
| 4,686,223 | 8/1987 | Cohnen et al. | 514/272 |
| 4,871,743 | 10/1989 | Taylor et al. | 514/272 |
| 4,880,812 | 11/1989 | Kelley | 514/272 |
| 4,920,125 | 4/1990 | Taylor et al. | 514/272 |
| 4,921,836 | 5/1990 | Bigham et al. | 514/19 |
| 4,971,973 | 11/1990 | Bigham et al. | 514/273 |
| 5,013,738 | 5/1991 | Taylor et al. | 514/272 |
| 5,262,385 | 11/1993 | Goh et al. | 504/239 |
| 5,426,110 | 6/1995 | Gossett et al. | 514/275 |
| 5,726,312 | 3/1998 | Varney et al. | 544/320 |

FOREIGN PATENT DOCUMENTS

| | | |
|---|---|---|
| 268377 | 5/1988 | European Pat. Off. . |
| 325343 | 7/1989 | European Pat. Off. . |
| 341837 | 11/1989 | European Pat. Off. . |

OTHER PUBLICATIONS

Okafor, "Studies in the Heterocyclic Series XVIII. Utilization of 4–Aminopyrimidine Chemistry in 1,4,7,9–Tetraazabenzo[b]phenothiazine Syntheses," J. Heterocyclic Chem. 17(7), 1587–92 (1980).

Mosmann, "Rapid Colorimetric Assay for Cellular Growth and Survival: Application to Proliferation and Cytotozicity Assays," J. Immunol. Meth. 65, 55–63 (1983).

Alley et al., "Feasibility of Drug Screening with Panels of Human Tumor Cell Lines Using Microculture Tetrazolium Assay," Cancer Res. 48–589–601 (1988).

Cleland, "The Kinetics of Enzyme–Catalyzed Reactions with Two or More Substrates of Products," Biochem. Biophys. Acta 67, 173–87 (1963).

Young et al., "An Antibody Probe to Determine the Native Species of Glycinamide Ribonucleotide Transformylase in Chicken Liver," Biochem 23, 3979–86 (1984).

Moran, "Folate antimetabolites inhibitory to de novo purine synthesis," New Drugs, Concepts & Results in Cancer Therapy, F. Muggia (ed.), 65–87 (1991).

Primary Examiner—Mukund J. Shah
Assistant Examiner—Deepak R. Rao
Attorney, Agent, or Firm—Finnegan, Henderson, Farabow, Garrett & Dunner, L.L.P.

[57] ABSTRACT

The present invention is directed to derivatives of 5-thia- and 5-selenopyrimidinone are useful as inhibitors of the enzyme glycimide ribonucleotide formyl transferase (GARFT) and amino imidozole carboxamide ribonucleotide formyl transferase (AICARFT), pharmaceutical compositions containing these derivatives, and methods of using these derivatives. The present invention is also directed to intermediates useful for preparing these derivatives and methods of preparing these intermediates.

33 Claims, No Drawings

1

ANTIPROLIFERATIVE SUBSTITUTED 5-THIAPYRIMIDINONE AND 5-SELENOPYRIMIDINONE COMPOUNDS

This application is a divisional of U.S. patent application Ser. No. 08/448,556, filed Jun. 7, 1995 now U.S. Pat. No. 5,739,141, which is the U.S. national phase Ser. application of PCT Application No. PCT/US93/11795, filed Dec. 10, 1993, which is a continuation-in-part of U.S. patent application Ser. No. 07/991,259, filed Dec. 16, 1992 now abandoned. Each of these applications is entirely incorporated herein by reference.

The present invention relates to certain substituted 5-thia- and 5-selenopyrimidinonyl compounds which inhibit the enzyme glycinamide ribonucleotide formyl transferase (GARFT), certain substituted 5-thia- and 5-selenopyrimidinonyl compounds which inhibit the enzyme amino imidazole carboxamide ribonucleotide formyl transferase (AICARFT), to intermediates thereof, to pharmaceutical compositions containing these compounds, and to the use thereof to inhibit the growth and proliferation of the cells of higher organisms and microorganisms such as bacteria, yeast and fungi. Such effects include antitumor, antiinflammatory, antipsoriatic and immunosuppressive activity. A process for the preparation of these compounds is also disclosed.

The large class of antiproliferative agents includes antimetabolite compounds. A particular subclass of antimetabolites known as antifolates or antifoles are antagonists of the vitamin folic acid. Typically, antifolates closely resemble the structure of folic acid and incorporate the characteristic P-benzoyl glutamate moiety of folic acid. The glutamate-moiety of folic acid takes on a double negative charge at physiological pH. Therefore, this compound and its analogs have an active energy driven transport system to cross the cell membrane and exert a metabolic effect.

GARFT and AICARFT are folate dependent enzymes in the de novo purine biosynthesis pathway. This pathway is critical to cell division and proliferation. Shutting down this pathway is known to have an antiproliferative effect, in particular, an antitumor effect. Thus, a number of folate analogs have been synthesized and studied for their ability to inhibit GARPT. A prototypic specific tight binding inhibitor of GARFT, 5,10-didedzatetrahydrofolic acid, has been reported to show antitumor activity. See F. M. Muggia, "Folate antimetabolites inhibitory to de novo purine synthesis" in *New Drugs, Concepts and Results in Cancer Chemotherapy*, pp.65–87, Kluwer Academic Publishers, Boston (1992).

The present invention introduces a novel class of 5-thia- or 5-selenopyrimidinonyl compounds containing a glutamic acid moiety. These compounds can be effective in inhibiting GARFT and/or AICARFT and the growth and proliferation of cells of higher organisms and of microorganisms such as bacteria, yeast and fungi. The invention further relates to pharmaceutical compositions containing these compounds or suitable salts thereof and the use of these compounds as inhibitors of the enzymes GARFT and/or AICARFT.

As stated above, compounds of the invention possess anti-proliferative activity, a property which may express itself in the form of anti-tumor activity. A compound of the invention may be active per se, or it may be a precursor which is converted in vivo to an active compound. Compounds of the present invention possess at least one chiral center. Thus compounds of the invention include mixtures of diastereomers or enantiomers, as well as diastereomers and enantiomers substantially free of other diastereomers or enantiomers.

Preferred compounds of the invention are active in inhibiting the growth of the L1210 cell line, a mouse leukemia cell line which can be grown in tissue culture. Compounds of the invention can also be active in inhibiting the growth of bacteria such as *Escherichia coli* gram negative bacteria which can be grown in culture.

The compounds according to the invention, as well as the pharmaceutically acceptable salts thereof, may be incorporated into convenient dosage forms such as capsules, tablets, or injectable preparations. Solid or liquid pharmaceutically acceptable carriers may also be employed. Solid carriers include starch, lactose, calcium sulphate dihydrate, terra alba, sucrose, talc, gelatin, agar, pectin, acacia, magnesium stearate and stearic acid. Liquid carriers include syrup, peanut oil, olive oil, saline solution and water.

The carrier or diluent may include any prolonged released material, such as glyceryl monostearate or glyceryl distearate, alone or with wax. When a liquid carrier is used, the preparation may be in the form of a syrup, elixir, emulsion, soft gelatin capsule, sterile injectable liquid (e.g. solution) or a non-aqueous or aqueous liquid suspension.

The pharmaceutical preparations (not necessarily the compounds or salts thereof per se) are prepared following conventional techniques of the pharmaceutical chemist involving steps such as mixing, granulating, and compressing when necessary for tablet forms, or mixing, filling and dissolving the ingredients as appropriate to give the desired products for oral, parenteral, topical, intravaginal, intranasal, intrabronchial, intraocular, intraaural and rectal administration.

The compositions of the invention may further comprise one or more other compounds which are anti-tumor agents such as: a mitotic inhibitor (for example: vinblastine); alkylating agents; dihydrofolate reductase inhibitors or TS inhibitors; antimetabolites (for example, 5-fluorouracil and cytosinearabinoside); intercalating antibiotics (for example, adriamycin and bleomycin); enzymes (for example, asparaginase); topoisonerase inhibitors (for example, etoposide); or biological response modifiers (for example, interferon).

The compositions of the invention may also comprise one or more other compounds including antibacterial, antifungal, antiparasitic, antiviral, antipsoriatic andanticoccidial agents. Exemplary antibacterial agents include, for example, sulfonamides such as sulfamethoxazole, sulfadiazine, sulfameter or sulfadoxine; dihydrofolic reductase inhibitors such as trimethoprim, bromodiaprim, or trimetrexate; penicillins; cephalosporins; aminoglycosides; bacteribstatic inhibitors of protein synthesis; the quinolone carboxylic acids and their fused isothiazolo-analogs.

Another aspect of the invention relates to a therapeutic process of inhibiting the growth and proliferation of cells of higher organisms and microorganisms which comprises administering to a host an effective amount of a compound according to the present invention. The compounds of the invention are particularly useful in the treatment of mammalian hosts such as human hosts and in the treatment of avian hosts. Therapeutic processes can comprise administering to a host an effective amount of a compound according to the present invention to inhibit GARFT and/or AICARFT.

Many of the antiproliferative drugs described herein or pharmaceutically acceptable salts thereof can be employed in the therapeutic process of the invention. The compounds may be administered in the form of a pharmaceutically acceptable composition comprising a diluent or carrier such as those described above.

Doses of the compounds preferably include pharmaceutical dosage units comprising an effective quantity of the active compound. An "effective quantity" means a quantity sufficient to inhibit the folate metabolic pathways and derive the beneficial effects therefrom through administration of one or more of the pharmaceutical dosage units.

An exemplary daily dosage unit for a vertebrate host comprises an amount up to one gram of active compound per kilogram of the host, preferably one half gram, more preferably 100 milligrams, and most preferably, about 50 milligrams or less per kilogram of the host weight. The selected dose may be administered to a warm-blooded animal or mammal, for example, a human patient in need of treatment mediated by folate metabolic pathways inhibition, by any known method of administrating the dose including topically as, for example, an ointment or cream; orally; rectally, for example, as a suppository; parenterally by injection; or continuously by intravaginal, intranasal, intravenous, intrabronchial, intraaural or intraocular infusion. For oral administration, one can use the compounds of the invention in ester or free acid form.

The compounds according to the present invention may be characterized as producing any one or more of an antiproliferative effect, antibacterial effect, an antiparasitic effect, an antiviral effect, an antipsoriatic effect, an antiprotozoal effect, an anticoccidial effect, an antiinflammatory effect, an immnunosupressive effect or an antifungal effect. The compounds can be especially useful in producing an antitumor effect in a vertebrate host harboring a tumor.

The present invention relates to antiproliferative compounds having the formula I

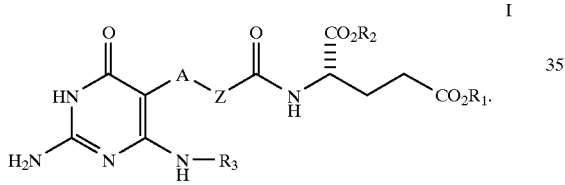

wherein:
A represents sulfur or selenium;
Z represents 1) a substituted or unsubstituted non-cyclic spacer which separates A from the carbonyl carbon of the amido group by 1 to 10 atoms, said atoms being independently selected from carbon, oxygen, sulfur, nitrogen, and phosphorous; 2) a substituted or unsubstituted mono or fused or nonfused poly-carbocyclic or heterocyclic radical; or 3) a combination of at least one of said non-cyclic spacer and at least one of said carbocyclic or heterocyclic radical, wherein when said non-cyclic spacer is bonded to A, said non-cyclic spacer separates A from one of said carbocyclic or heterocyclic radicals by 1 to 10 atoms and further wherein when said non-cyclic spacer is bonded to —C(O)—, said non-cyclic spacer separates —C(O)— from one of said carbocyclic or heterocyclic radicals by 1 to 10 atoms;
$R_1$ and $R_2$ represent, independently, H or $C_1$ to $C_6$ alkyl or other readily lyzable, preferably hydrolyzable, groups; and
$R_3$ represents H or a straight, branched or cyclic $C_1$ to $C_6$ alkyl group (cyclic obviously applies only to $C_3$ to $C_6$ alkyl groups) optionally carrying one or more halogen, hydroxyl or amine groups; or a pharmaceutically acceptable salt thereof.

A preferred subgenus of the compounds of the invention has the formula II

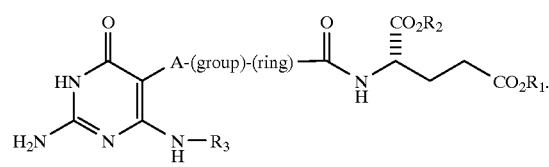

wherein:
A is sulfur or selenium;
(group) represents a non-cyclic spacer which separates A from (ring) by 1 to 5 atoms, said atoms being independently selected from carbon, oxygen, sulfur, nitrogen and phosphorus and optionally carrying one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$)alkyl groups, $C_2$ to $C_6$ alkynyl groups, acyl groups, halogen, amino groups, hydroxyl groups, nitro groups or mercapto groups, monocyclic carbo- or heterocyclic rings, and fused or non-fused poly-carbocyclic or poly-heterocyclic rings;
(ring) represents one or more of a substituted or unsubstituted monocyclic, carbo- or heterocyclic ring or a fused or non-fused polycarbocyclic or heterocyclic ring optionally substituted with one or more substituents selected from those recited for (group);
$R_1$ and $R_2$ represent, independently, hydrogen, $C_1$ to $C_6$ alkyl or other readily lyzable, preferably hydrolyzable, groups; and
$R_3$ represents hydrogen or a straight, branched or cyclic $C_1$ to $C_6$ alkyl group (obviously cyclic only involves $C_3$ to $C_6$ alkyl groups) optionally carrying halogen, hydroxyl, or amine substitution; or a pharmaceutically acceptable salt thereof.

In a preferred embodiment of the compound of formula I, the moiety Z is represented by Q—X—Ar wherein:
Q represents a $C_1$–$C_5$ alkylene, or a $C_2$–$C_5$ alkenylene or alkynylene radical optionally carrying one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$)alkyl groups, $C_2$ to $C_6$ alkynyl groups, acyl groups, halogen, amino groups, hydroxyl groups, nitro groups or mercapto groups, monocyclic carbo- or heterocyclic rings, and fused or non-fused poly-carbocyclic or poly-heterocyclic rings;
X represents a methylene, monocyclic carbo- or heterocyclic ring, sulfur, oxygen or amino radical, optionally carrying one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$)alkyl groups, $C_2$ to $C_6$ alkynyl groups, acyl groups, halogen, amino groups, hydroxyl groups, nitro groups or mercapto groups, monocyclic carbo- or heterocyclic rings, and fused or non-fused poly-carbocyclic or poly-heterocyclic rings; and
Ar represents a monocyclic carbo- or heterocyclic aromatic ring or a bicyclic carbo- or heterocyclic ring, all or a portion of which may be aromatic, and wherein the Ar may, be fused to the monocyclic carbo- or heterocyclic ring of X, and wherein the Ar optionally carries one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$)alkyl groups, $C_2$ to $C_6$ alkynyl groups, acyl groups, halogen, amino groups, hydroxyl groups, nitro groups or mercapto groups, monocycliccarbo- or heterocyclic rings, and fused or non-fused poly-carbocyclic or poly-heterocyclic rings; or a pharmaceutically acceptable salt thereof.

In a preferred embodiment of the compound of formula II, the moiety (group) represents a $C_1$ to $C_4$ alkylene group and the moiety (ring) represents a substituted or unsubstituted, fused or non-fused carbocyclic or heterocyclic bicyclic ring system, or a substituted or unsubstituted, carbocyclic or heterocyclic monocyclic ring system, or at least two monocyclic ring systems linked by a single bond, said monocyclic ring systems being independently substituted or unsubstituted.

Another preferred embodiment of the invention has the formula III wherein:
A represents sulfur or selenium;
Ar represents an unsubstituted phenylene or thienylene radical;
$R_1$ and $R_2$ represent, individually, hydrogen or $C_1$ to $C_6$ alkyl or other readily lyzable, preferably hydrolyzable, groups;
$R_3$ represents hydrogen or a straight, branched or cyclic: $C_1$–$C_6$ alkyl group (obviously, when the alkyl is cyclic, $C_3$–$C_6$ is intended), optionally carrying one or more halogen, hydroxyl or amine groups; or
a pharmaceutically acceptable salt thereof.

Preferably, $R_3$ in formula X is hydrogen. A in formula X is preferably —S—. Preferably, $R_1$ and $R_2$ independently represent hydrogen, methyl and ethyl in formula X.

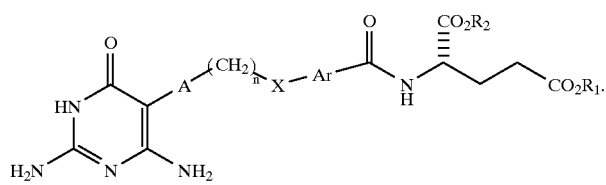

III wherein n is an integer from 0 to 5, A represents sulfur or selenium, X is methylene, monocyclic carbo- or heterocyclic ring, O, S, or —NH—, Ar is an aromatic radical, wherein Ar can form a fused bicyclic ring system with said ring of X, and $R_1$ and $R_2$, which can be the same or different, are hydrogen or alkyl radicals having 1 to 6 carbon atoms or a pharmaceutically acceptable salt thereof.

Ar in formula III can be any substituted or unsubstituted 5 or 6 membered aromatic ring such as, for example, 3-methyl-2,5-thienyl, 4-methyl-2,5-thienyl, 3-ethyl-2,5-thienyl,1,4-phenylene, 1,3-phenylene, 2,5-thienyl, 2,4-thienyl, 2,5-pyrrole, 2,4-pyrrole, 2,5-furyl, 2,4-furyl, 2,5-pyridyl, 2,4-pyridyl, 2-methyl-1,4-phenylene, and the like.

Although the compounds are depicted throughout this description in the formulae in the 4-oxo form and are referred to as such throughout this description, the oxo group exists in tautomeric equilibrium with the corresponding 4-hydroxy group and it will be understood that in each case the tautomeric hydroxyl form is also indicated.

The compounds of formula I in which each of $R_1$ and $R_2$ is hydrogen are active anti-tumor and antiproliferative compounds. The compounds of formula I wherein $R_1$ and $R_2$ are lower alkyl groups or other readily lyzable groups are novel intermediates for forming the free glutamic acid forms of the compounds and can also be metabolized in vivo to polyglutamates and thus act as prodrugs. The invention also relates to compounds useful as AICARFT inhibitors of the formula X The compounds of formula X in which each of $R_1$ and $R_2$ is hydrogen are active anti-tumor and antiproliferative compounds. The compounds of formula X wherein $R_1$ and $R_2$ are lower alkyl groups or other readily lyzable groups are novel intermediates for forming the free glutamic acid forms of the compounds and can also be metabolized in vivo to polyglutamates and thus act as prodrugs.

As discussed above, the invention also includes pharmaceutically acceptable salts, including, for example, alkaline metal, alkaline earth metal, other non-toxic metals, ammonium and substituted ammonium salts of the glutamic acid embodiments of the invention such as, but not limited to, the sodium, potassium, lithium, calcium, magnesium, aluminum, zinc, ammonium, trimethyl ammonium, triethyl ammonium, tetrabutyl ammonium, pyridinium and substituted pyridinium salts.

Novel compounds of the formula V

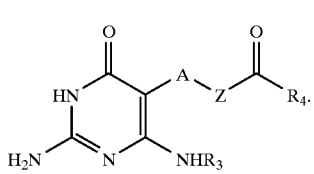

V wherein:
A represents sulfur or selenium;

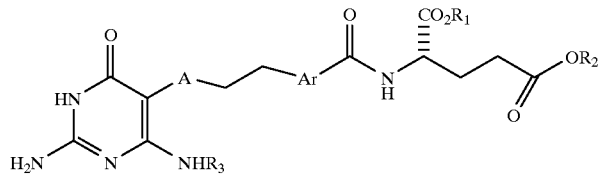

X

Z represents 1) a substituted or unsubstituted non-cyclic spacer which separates A from the carbonyl carbon of the amido group by 1 to 10 atoms, said atoms being independently selected from carbon, oxygen, sulfur, nitrogen and phosphorous; 2) a substituted or unsubstituted mono- or fused or nonfused poly-carbocyclic or heterocyclic radical; or 3) a combination of at least one of said non-cyclic spacer and at least one of said carbocyclic or heterocyclic radical; wherein said non-cyclic spacer separates A from one of said carbocyclic or heterocyclic radicals by 1 to 10 atoms; and $R_3$ represents H or a straight, branched or cyclic ($C_1$ to $C_6$) alkyl group (obviously, when the alkyl is cyclic, $C_3$–$C_6$ is intended), optionally carrying one or more hydroxyl or amine groups;

$R_4$ represents hydroxy, ($C_1$ to $C_6$) alkyloxy group optionally carrying one or more hydroxyl or amine groups, or a protected or unprotected amino acid linked to the acyl group of formula V by the amine portion of the amino acid;

or a pharmaceutically acceptable salt thereof;

can be prepared by reacting a compound having the

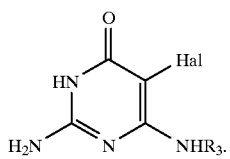

VI wherein hal is bromine, chlorine, fluorine, or iodine, preferably bromine, and $R_3$ is as defined above with a compound having the formula IV

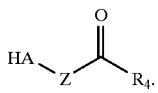

IV wherein A, Z, and $R_4$ are as defined above, in the presence of another base, preferably a non-nucleophilic auxiliary base, in a solvent in which at least one of the reactants is at least partially soluble under conditions sufficient to obtain the compound of formula V.

In a preferred embodiment of the compound of formula V, Z represents —$(CH_2)_n$—X—Ar— wherein n is an integer from 0 to 5, A represents sulfur, X is methylene, monocyclic carbo- or heterocyclic ring, O, S, or —NH—, and Ar is an aromatic radical, wherein Ar can form a fused bicyclic ring system with said ring of X.

The reaction is preferably carried out in a suitable solvent in which at least one or both reactants are soluble at the reaction temperature. The solvent and the reaction environment are preferably purged of oxygen prior to introduction of the reactants by bubbling an inert gas, such as argon or nitrogen, through the solvent. Bubbling of the inert gas is preferably continued until the reaction has gone to completion and been quenched, such as by pouring into water. Suitable preferred solvents are dipolar aprotic solvents such as, e.g., dimethylsulfoxide, N,N-dimethylformamide, N,N-dimethylacetamide, or N-methyl-2-pyrolidinone.

The basic medium is preferably provided via a non-nucleophilic auxiliary base which is defined as a base capable of neutralizing hydrogen halide, preferably hydrogen bromide, gas generated by the substitution reaction. The base is preferably an alkali or earth metal carbonate or a trialkylamine such as, e.g., trimethylamine, triethylamine or diisopropylethylamine.

A more specific method for conducting the reaction of compounds of the formulae IV and VI is to suspend the compound of formula VI, preferably, 5-bromo-2,6-diamino-4(3H)-oxo-pyrimidine, in the solvent; compound of the formula IV and the auxiliary base are then added sequentially. The reaction vessel is then immersed in an oil bath which has been heated to the appropriate temperature (20–200°, preferably 70–120° C.). The reaction mixture is stirred at this temperature for the requisite length of time (usually 30–330 minutes), then cooled to room temperature and poured into water. The product is then isolated by filtration or extraction with an organic solvent and purified either by recrystallization or by chromatography.

The compound of the formula V can be hydrolyzed, in basic medium, to its free carboxylic acid form, peptide coupled, by means well-known to those skilled in the art, with a glutamic acid diester hydrochloride and, finally, hydrolyzed to the free glutamic acid form depicted in formula I ($R_1$ and $R_2$=H). Detailed syntheses for various compounds of formula I will be presented in the examples that follow.

Specific examples of novel compounds of formula I include:

N-[4-(3-[2,6-diamino-4(3H)-oxopyrimidin-5-yl)thio]propyl)benzoyl-(S)-glutamic acid (Example 2);

N-[4-(N-[2-([2,6-diamino-4(3H)-oxopyrimidin-5-yl]thio)ethyl]amino)benzoyl]-S-glutamic acid (Example 5);

N-((4-[2-([2,6-diamino-4(3H)-oxopyrimidin-5-yl]thio)ethyl]thio)benzoyl]-S-glutamic acid (Example 4);

N-[2-(5-[3-([2,6-diamino-4(3H)-oxopyrimidin-5-yl]thio)propyl]-thienoyl)]-(S)-glutamic acid (Example 3);

N-[5-(3-[2,6-Diamino-4(3H)-oxopyrimidin-5-yl)thio]-propyl)-3-methyl-thieno-2-yl]-L-glutamic acid (Example 6);

N-[5-(3-[2,6-Diamino-4(3H)-oxopyrimidin-5-yl)thio]-propyl)-4-methyl-thieno-2-yl}-L-glutamic acid (Example 7);

N-(6[([2,6-diamino-4(3H)-oxopyrimidino-5-yl]thio)-methyl]-4,5,6,7-tetrahydrobenzothieno-2-yl)-S-glutamic acid (Example 8);

N-(5-[2-([2,6-Diamino-4(3H)-oxopyrimidin-5-yl]thio)ethyl]thieno-2-yl)-L-glutamic acid (Example 9); and N-(4(4-[2-([2,6-Diamino-4(3H)-oxopyrimidin-5-yl]thio)ethyl]benzoyl)-L-glutamic acid (Example 10).

It is to be understood that application of the teachings of the present invention to a specific problem or environment will be within the capabilities of one having ordinary skill in the art in light of the teachings contained herein. Examples of the products of the present invention and representative processes for their preparation and recovery appear in the following examples.

EXAMPLE 1

Synthesis of 5-bromo-2,6-diamino-4(3H)-oxo-pyrimidine

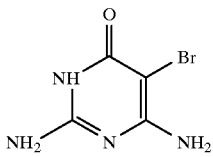

This compound was prepared according to a procedure described by C. O. Okafor, J. Heterocyclic Chem., 17, 1587 (1980).

Eighty mmol (10.09 g) of commercially available 2,6-diamino-4(3H)-pyrimidinone was deposited in a one liter flask suspended in a mixture of 60 ml of methanol and 60 ml of water. This suspension was vigorously stirred and 12 grams of sodium bicarbonate was added in a single portion. Eight ml (155 mmole) of liquid bromine was added dropwise to the reaction flask over a 40-minute interval. An additional 30 ml of 50% aqueous methanol was then added to the reaction mixture to facilitate stirring. After stirring for a further 30 minutes, an additional 8 grams of sodium bicarbonate was added in a single portion. The resultant reaction mixture was stirred for 75 minutes and left standing at room temperature overnight. The product was collected by filtration and recrystallized from 300 ml of water, yielding 6.4 grams (39% yield) of yellow needles having a M.P. of 242° C. (decomposed).

EXAMPLE 2

Synthesis of N-(4-(3-[2,6-diamino-4(3H)-oxopyrimidin-5-yl)thio]propyl)benzoyl-(S)-glutamic Acid This compound of formula III wherein A is sulfur, n=2, x=—$CH_2$—, Ar=phenylene, and $R_1$ & $R_2$=hydrogen was synthesized via the following 10-step process.

a. Methyl-4-iodobenzoate

Fifty (50) mmol (12.4 g) of commercially available 4-iodobenzoic acid was dissolved in 200 ml of tetrahydrofuran and then added to an ether solution containing freshly prepared diazomethane. The excess diazomethane was subsequently consumed by addition of glacial acetic acid and the resultant solution was concentrated in vacuo. The residue thus obtained was partitioned between ethyl acetate and saturated $NaHCO_3$. The layers were separated and the aqueous phase was extracted with 100 ml of ethyl acetate. The organic extracts were combined, dried over $Na_2SO_4$, and concentrated in vacuo, yielding 13.01 grams (99.3% yield) of a yellow solid which melted at 111° C.

The following analyses indicate that methyl 4-iodobenzoate were obtained.

HNMR (300 MHz, GE QE-300, $CDCl_3$) δ=7.80 (2H, d, J=8.6 Hz); 7.74 (2H, d, J=8.6 Hz); 3.91 (3H, s). Elemental Analysis: Calculated as $C_8H_7O_2I$: C=36.37; H=2.69 and I=48.43 Found: C=36.91; H=2.74 and I=48.23 b. Methyl 4-(3-hydroxypropynyl)benzoate

Methyl 4-iodobenzoate (9.0 g, 34.4 mmol) was dissolved in 90 ml of diethylamine. The solution was stirred vigorously and, sequentially, 121 milligrams of bis(triphenylphosphine) palladium chloride and 65 milligrams of cuprous iodide were added, each in a single portion, followed by 1.93 grams of propargyl alcohol. The resultant mixture was stirred for about 20 hours at room temperature in an argon atmosphere. At the end of this period, diethylamine was removed by concentration in vacuo. The residue was diluted with 200 ml of water and extracted three times with 100 ml of benzene and 75 ml of ethyl acetate. The organic extracts were combined, dried over $Na_2SO_4$, and concentrated in vacuo, yielding a brown solid. This crude residue was purified by flash chromatography. Elution with a 2 to 1 (V:V) mixture of hexane and ethyl acetate yielded 5.44 grams (83% yield) of a pale yellow solid melting at 81 to 82° C.

The following analyses were obtained for this material, indicating that it was methyl 4-(3-hydroxy propynyl) benzoate:

NMR ($CDCl_3$) δ=7.98 (2H, d, J=8.3 Hz), 7.49 (2H, d, J=8.3 Hz), 4.52 (2H, s), 3.92 (3H,s); Anal. ($C_{11}H_{10}O_3$) C,H c. Methyl 4-(3-hydroxypropyl)benzoate Three grams (15.8 mmol) of methyl 4-(3-hydroxy propynyl) benzoate was dissolved in 200 ml of ethanol in a Parr flask and 0.3 g (10% wt. eq.) of 5% Pd/C was added. This mixture was shaken under 45 psi of hydrogen for 3.5 hours. The crude reaction mixture was filtered through a pad of Celite® and the filtrate was then concentrated, in vacuo, yielding a green oil which was purified by vacuum flash chromatography. Elution with a 2 to 1 (V:V) mixture of hexane and ethyl acetate yielded 2.9 grams (95% yield) of a yellow oil.

The following analyses were obtained for this material, indicating that it was methyl 4-(3-hydroxypropyl) benzoate:

NMR ($CDCl_3$) δ=7.96 (2H, d, J=8.3 Hz), 7.27 (2H, d, J=8.3 Hz), 3.90 (3H, s), 3.68 (2H, J=6.4 Hz), 2.77 (2H, t, J=7.5 Hz), 1.91 (2H, tt, J=6.4, 7.5 Hz); Anal. ($C_{11}H_{14}O_3.0.3H_2O$) C,H d. Methyl 4-3(bromopropyl)benzoate Methyl 4-(3-hydroxypropyl) benzoate, (3.49 g, 18 mmol) and 4.21 grams of carbon tetrabromide were dissolved in 25 milliliters of methylene chloride. This solution was stirred vigorously and cooled to about 0° C. centigrade. Triphenyl phosphine (5.67 grams dissolved in 25 ml of methylene chloride) was added dropwise to this solution over a 10 minute period, with the reaction temperature holding at about 0°. The resultant yellow solution was stirred at 0° for about 30 minutes, then overnight at room temperature. The crude reaction mixture was concentrated in vacuo and the residue was purified by flash chromatography. Elution with 9 to 1 (v:v) hexane ethyl acetate yielded 4.38 grams (95% yield) of product as a yellow oil.

The following analyses were obtained for this material, indicating that it was methyl (4-(3-bromopropyl) benzoate:

NMR ($CDCl_3$) δ=7.97 (2H, d, J=8.2 Hz), 7.27 (2H, d, J=8.2 Hz), 3.91 (3H, s), 3.39 (2H, t, J=6.5 Hz), 2.84 (2H, t, J=7.4 Hz), 2.18 (2H, tt, J=6.5, 7.4 Hz); Anal. ($C_{11}H_{13}O_2Br$) C,H,Br e. Methyl 4-[3-(acetylthio)propyl]benzoate Five (5) mmol (1.29 grams) of methyl 4-(3 bromopropyl) benzoate was dissolved in 40 ml of acetone and vigorously agitated while 10 mmol (1.14 grams) of potassium thioacetate was added in a single portion. The mixture was heated at reflux for 35 minutes, then returned to room temperature and filtered. The filter cake was washed twice with acetone. The filtrate and washings were combined and concentrated under vacuum. The residue was partitioned between ether and water (25 ml each). The layers were separated and the aqueous phase extracted with 25 ml of ether. The organic extracts were combined, dried over $Na_2SO_4$, and concentrated in vacuo, yielding a red oil. This oil was purified by flash chromatography. Elution with hexane/ethyl acetate (9 to 1 V:V) yielded 1.22 g (97% yield) of an amber colored oil.

The following analyses were obtained for this material indicating that it was methyl 4-[3-(acetylthio)propyl] benzoate:

NMR (CDCl$_3$) δ=7.95 (2H, d, J=8.3 Hz), 7.24 (2H, d, J=8.3 Hz), 3.90 (3H, s), 2.88 (2H, t, J=7.2 Hz), 2.74 (2H, t, J=7.7 Hz), 2.34 (3H, s), 1.91 (2H, tt, J=7.2, 7.7 Hz); Anal. (C$_{13}$H$_{16}$O$_3$S) C,H,S f. Methyl 4-(3-thiopropyl)benzoate One ml (1.1 gram) of acetyl chloride was added slowly to 10 ml of methanol in a 100 ml flask. This solution was rapidly stirred and to it was added a solution of methyl 4-[3-(acetylthio)propyl] benzoate in 5 ml of methanol. The reaction mixture was heated at reflux for two hours, then cooled to room temperature. The crude reaction mixture was diluted with 10 ml of water. Methanol was removed by concentration under vacuum, and the aqueous residue was extracted twice with 25 ml of ether. The organic extracts were combined, dried over Na$_2$SO$_4$, and concentrated under vacuum, yielding 815 milligrams (97.3% yield) of an amber colored oil.

The following analyses were obtained for this material, indicating that it is the desired methyl 4-(3-thiopropyl) benzoate:

NMR (CDCl$_3$) δ=7.96 (2H, d, J=8.2 Hz), 7.25 (2H, d, J=8.2 Hz), 3.90 (3H, s), 2.79 (2H, t, J=7.6 Hz), 2.57–2.50 (2H, m), 2.00 (2H, m), 1.37 (1H, t, J=7.9 Hz); Anal. (C$_{11}$H$_{14}$O$_2$S) C,H,S g. Methyl 4-(3-[2,6-diamino-4(3H)-oxopyrimidin-5-yl)thio] propyl)benzoate Argon was bubbled through a slurry of 1.01 grams (4.9 mmol) of 5-bromo-2,6-diamino-4(3H)pyrimidinone in 15 ml of DMF. To this slurry was added a solution of 1.11 gram (5.3 mmol) of methyl 4-(3-thiopropyl)benzoate in 10 ml of DMF and 1.8 ml (1.34 g) of diisopropyethylamine. This mixture was heated at 100° C. for 30 minutes, then poured over ice. The resultant precipitate was collected by filtration, washed twice with 30 ml of H$_2$O, then twice with 30 ml of ether, yielding 711 mg of a white powder (73% yield) melting at 248 to 251° C. (decomposed).

The following analyses indicated that this material was the desired 4-(3-[(2,6-diamino-4(3H)-oxopyrimidin-5-yl) thio)propyl) benzoate:

NMR (DMSO-d6) δ=9.95 (1H, s), 7.84 (2H, d, J=8.2 hz), 7.33 (2H, d, J=8.2 hz), 6.28 (4H, broad), 3.82 (3H, s), 2.76 (2H, t, J=7.2 Hz), 2.42 (2H, t, J=7.0 Hz), 1.70 (2H, tt, J=7.0, 7.2 hz); Anal. (C$_{15}$H$_{18}$N$_4$O$_3$S·0.3H$_2$O)C,H,N,S h. 4-(3-[2,6-diamino-4(3H)-oxopyrimidin-5-yl)thio]propyl) benzoic acid A suspension of 669 mg (2 mmol) of 4-(3-[(2,6-diamino-4(3H)-oxopyrimidin-5yl)thio]propyl)benzoate in 30 ml of 1N NaOH was stirred overnight at room temperature, then filtered. The filtrate was acidified to pH 5.0 with acetic acid. The precipitate that formed was collected by filtration and washed 3 times with 5 ml of H$_2$O yielding 589 mg (91.9% yield) of an off-white powder product.

The following analyses indicated that this was the desired 4-(3-[(2,6-diamino-4(3H)-oxopyrimidin-5yl)thio]propyl) benzoic acid:

NMR (DMSO-d6) δ=12.72 (1H, broad), 9.97 (1H, broad), 7.82 (2H, d, J=8.1 Hz), 7.29 (2H, d, J=8.1 Hz), 6.29 (4H, broad) 2.74 (2H, t, J=7.2 Hz), 2.43 (2H, t, J=7.0 Hz), 1.70 (2H, tt, d=7.0, 7.2 Hz) Anal. (C$_{14}$H$_{16}$N$_4$O$_3$S) C,H,N,S i. Diethyl N-[4-(3-[(2,6-diamino-4(3H)-oxopyrimidin-5-yl) thio]propyl)benzoyl]-S-glutamate 4-(3-[(2,6-diamino-4(3H)-oxopyrimidin-5-yl)thio] propyl) benzoic acid (577 mg) was dissolved in 40 ml of 1-methyl-2-pyrrolidinone. This mixture was vigorously stirred and 920 milligrams of 4-methyl morpholine were added followed by 723 milligrams of phenyl N-phenylphosphoroamidochloridate in a single portion. The mixture was stirred under an argon atmosphere at room temperature for 60 minutes followed by the addition of 863 milligrams of S-glutamic acid diethyl ester hydrochloride. This mixture was left stirring overnight under argon 20 hours, then concentrated in vacuo. The residue obtained was partitioned between 30 ml of water and 30 ml of chloroform. The layers were separated and the aqueous phase was extracted with 30 ml of chloroform. The combined organic extracts were washed with 30 ml of H$_2$O and dried over MgSO$_4$ then concentrated in vacuo to yield a yellow gum, which was purified by flash chromatography. Elution with 5% methanol in ethyl acetate yielded 212 mg of a white solid melting at 78–81° C.

The following analyses indicated that this material was the desired diethyl N-[4-(3-[(2,6-diamino-4(3H)-oxopyrimidin-5yl)thio]propyl)benzoyl]-S-glutamate.

NMR(CDCl$_3$) δ=7.67(2H, d, J=8.1 Hz), 7.28(1H, d, J=8.0 Hz), 7.16(2H, d, J=8.1 Hz), 6.64(2H, br s), 5.84(2H, br s), 4.78(1H, ddd, J=5.0, 8.0, 12.8 Hz), 4.21(2H, q, J=7.1Hz), 4.09(2H, q, J=7.1 Hz), 2.64(2H, t, J=7.3 Hz), 2.57–2.25(4H, m), 2.21–2.09(2H, m), 1.83(2H, tt, J=7.0, 7.3 Hz), 1.29(3H, t, J=7.1 Hz), 1.21(3H, t, J=7.1 Hz); Anal. (C$_{23}$H$_{31}$N$_5$O$_6$S) C,H,N,S j. N-[4-(3-[(2,6-diamino-4(3H)-oxopyrimidin-5yl) thio] propyl)benzoyl]-S-glutamic acid A solution of 192 mg (0.4 mmol) of diethyl N-[4-(3-[(2,6 thiamino-4(3H)-oxopyrimidin-5-yl)thio]propyl)benzyl]-S-glutamate in 15 ml of 1N NaOH was stirred at room temperature for about 70 hours, then neutralized with 6N HCl. The precipitate that formed was collected by filtration and washed 3 times with 10 ml of H$_2$O yielding 147 mg of a white solid which melted at 205–206° C.

The following analyses indicate that the product was the desired N-[4-(3-[(2,6-diamino-4(3H)-oxopyrimidin-5yl) thio]-propyl) benzoyl]-S-glutamic acid:

NMR(DMSO-d6) δ=12.34(2H, broad), 9.96(1H, broad), 8.51(1H, d, J=7.7 Hz), 7.76(2H, d, J=8.2 Hz). 7.27(2H, d, J=8.2 Hz), 6.29(4H, br s), 4.37(1H, ddd, J=4.8 7.7, 9.7 Hz), 2.73(2H, t, J=7.2 Hz), 2.43(2H, t, J=6.9 Hz), 2.34(2H, t, J=7.9 Hz),2.11–2.01(1H, m), 1.99–1.89 (1H, m), 1.69 (2H, tt, J=6.9, 7.2 Hz); Anal. (C$_{19}$H$_{23}$N$_5$O$_6$S) C,H,N,S

EXAMPLE 3

Synthesis of N-[2-(5-[3-([2,6-diamino-4(3H)-oxopyrimidin-5-yl]thio)pyropyl]-thienoyl)]-(S)-glutamic acid This compound of formula III, wherein A is sulfur, n=2, x=—CHd$_2$—,Ar=2,5-thienyl, and R$_1$ and R$_2$=H, was synthesized by the following process.

a) 5-Bromothioohene-2-carboxylic acid

To a solution of 5-bromothiophene-2-carboxaldehyde (12 ml, 19.28 g,0.1 mol) in acetone (400 ml), was added, portionwise, KMnO$_4$ (19.57 g, 0.12 mol) over a 10 minute interval. The mildly exothermic reaction was left stirring, with no external temperature control, overnight. The crude reaction mixture was filtered and the filter-cake extracted, alternately, with 1N NaOH (3×150 ml) and warm water (2×200 ml). The combined aqueous extracts were washed with ether (100 ml), then acidified by addition of conc. HCl. The precipitate that formed was collected by filtration to yield the product as a yellow solid (17.31 g, 83% yield) which melted at a 140° C.

The following analyses indicate that the product obtained was 5-bromothiophene-2-carboxylic acid:

NMR(CDCl$_3$) δ=7.64(1H, d, J=4.0 Hz), 7.12(1H, d, J=4.0 Hz) Anal. (C$_5$H$_3$O$_2$SBr) C,H,S,Br b) Methyl 5-bromothiophene-2-carboxylate A solution of 5-bromothiophene-2-carboxylic acid (17.6 g, 85 nmol) in ether (200 ml) was combined with an ether solution containing excess diazomethane. The excess CH$_2$N$_2$ was consumed by addition of glacial acetic acid and the resultant solution was dried over K$_2$CO$_3$ and MgSO$_4$, then concentrated, in vacuo, to provide the product as a yellow solid (18.72 g, 100% yield) mp 58°–59°

The following analyses indicate that the product was methyl 5-bromothiophene-2-carboxylate:

NMR(CDCl$_3$) δ=7.55(1H, d, J=4.0 Hz), 7.07(1H, d, J=4.0 Hz), 3.87(3H, s); Anal. (C$_6$H$_5$O$_2$SBr) C,H,S,Br c) Methyl 5-(3-hydroxypropynyl thiophene-2-carboxylate This product was prepared using the procedure described in Example 2(b). From 11.05 grams (50 mmol) of methyl 5-bromothiophene-2-carboxylate there was obtained 7.41 grams (76% yield) of a yellow solid melting at 66 to 68° C.

The following analyses indicate that the product was methyl 5-(3-hydroxypropynyl)thiophene-2-carboxylate:

NMR(CDCl$_3$) δ=7.64(1H, d, J=3.9 Hz), 7.15(1H, d, J=3.9 Hz), 4.52(2H, broad), 3.88(3H, s), 1.84(1H, broad) Anal. (C$_9$H$_8$O$_3$S) C,H,S d) Methyl 5-(3-hydroxyoropyl)thiophene-2-carboxylate To a solution of methyl 5-(3-hydroxypropynyl)thiophene-2-carboxylate, (7.41 g, 38 mmol) in THF (140 ml) was added 2,4,6-triisopropylbenzenesufonyl hydrazide (96.13 g, 0.32 mol) in four portions at 90 minute intervals. After the reaction had been heated at reflux for a total of 6.5 hours, the solvent was removed by concentration, in vacuo. The residue obtained was partitioned between 0.5N NaOH (700 ml) and ether (500 ml). The layers were separated and the aqueous phase extracted with ether (250 ml). The combined organic extracts were washed with 0.5N NaOH (2×150 ml), dried over Na$_2$SO$_4$ and concentrated, invacuo, to give an oil which was purified by flash chromatography. Elution with hexane/EtOAc (2:1) yielded the product as a yellow oil (3.67 g.48% yield).

The following analyses indicate that the product was methyl 5-(3-hydroxypropyl)thiophene-2-carboxylate:

NMR(CDCl$_3$) δ=7.64(1H, d, J=3.8 Hz), 6.82(1H, d, J=3.8 Hz), 3.86(3H, s), 3.71(2H, t, J=6.2 Hz), 2.96(2H, t, J=7.6 Hz), 1.96(2H, tt, J=6.2, 7.6 Hz); Anal. (C$_9$H$_{12}$O$_3$S) C,H,S e) Methyl 5-(3-bromopropyl)thiophene-2-carboxylate This product was prepared using the procedure described for Example 2(d). From 3.67 grams (18.3 mmol) of methyl 5-(3-hydroxypropyl)thiophene-2-carboxylate there was obtained 4.56 grams (95% yield) of a yellow oil.

The following analyses indicate that the product was methyl 5-(3-bromopropyl)thiophene-2-carboxylate:

NMR(CDCl$_3$) δ=7.64(1H, d, J=3.7 Hz, 6.85(1H, d, J=3.7 Hz).3.86(3H, s),3.43(2H, t, J=6.4 Hz, 3.03 (2H, t, J=7.2 Hz), 2.22 (2H, tt, J=6.4, 7.2 Hz) Anal. (C$_9$H$_{11}$O$_2$SBr) C,H,S,Br f) Methyl 5-[3-(acetylthio)propyl]thiophene-2-carboxylate This product was prepared using the procedure described for Example 2(e). From 5.01 grams (19 mmol) of methyl 5-(3-bromopropyl)thiophene-2-carboxylate there was obtained 4.54 grams (92% yield) of a yellow oil.

The following analyses indicate that that product was methyl 5-[3-(acetylthio)propyl]thiophene-2-carboxylate:

NMR(CDCl$_3$) δ=7.63(1H, d, J=3.7 Hz), 6.81(1H, d, J=3.7 Hz), 3.86(3H, s), 2.91 (4H, t, J=7.3 Hz), 2.34 (3H, s), 1.97 (2H, pentet, J=7.3 Hz); Anal. (C$_{11}$H$_{14}$O$_3$S$_2$) C,H,S g) Methyl 5-(3-thiopropyl)thiophene-2-carboxylate This product was prepared using the procedure described for example 2 (f). From 4.29 grams (16.6 mmol) of methyl 5-[3-(acetylthio)propyl]thiophene-2-carboxylate there was obtained 3.35 grams (93% yield) of an orange-colored oil.

The following analyses indicate that that product was methyl 5-(3-thiopropyl)thiophene-2-carboxylate:

NMR(CDCl$_3$) δ=7.63(1H, d, J=3.7 Hz), 6.81(1H, d, J=3.7 Hz), 3.86(3H, s), 2.98(2H, t, J=7.4 Hz),2.57(2H, dt, J=8.0, 7.1 Hz), 1.99(2H, tt, J=7.1, 7.4 Hz), 1.36(1H, t, J=8.0 Hz); Anal. (C$_9$H$_{12}$O$_2$S$_2$) C,H,S h) Methyl 5-(3-[(2,6-diamino-4(3H)-oxopyrimidin-5-yl)thio]propyl)thiophene-2-carboxylate This material was prepared using the procedure described in example 2(g). From 3.03 grams (14 mmol) of methyl-5-(3-thiopropyl)thiophene-2-carboxylate there were obtained 1.88 grams (44% yield) of an off-white solid melting at 196° C. (dec.).

The following analyses indicate that the product was methyl 5-(3-[(2,6-diamino-4(3H)-oxopyrimidin-5-yl)thio]-propyl)thiophene-2-carboxylate.

NMR(DMSO-d6) δ=9.96(1H, br s), 7.61(1H, d, J=3.8 Hz), 6.93(1H, d, J=3.8 Hz), 6.29(4H, broad), 3.77(3H, s), 2.97(2H, t, J=7.5 Hz), 2.45(2H, t, J=6.8 Hz), 1.74(2H, tt, J=6.8, 7.5 Hz); Anal. (C$_{13}$H$_{16}$N$_4$O$_3$S$_2$) C,H,N,S i) 5-(3-[(2,6-Diamino-4(3H)-oxopyrimidin-5-yl)thio]propyl thiophene-2-carboxylic acid This material was prepared using the procedure described for example 2 (h). By saponification of 1.7 grams (5 mmol) of methyl 5-(3-[(2,6-diamino-4-(3H)-oxopyrimidin-5-yl)thio]propyl)thiophene-2-carboxylate there was obtained 1.53 grams (94% yield) 5-(3-[(2,6-diamino-4(3H)-oxopyrimidin-5-yl)thio]propyl)thiophene-2-carboxylic acid as a yellow powder melting at 254° C. (dec.).

The following analysis indicate that that product was the 5-(3-[(2,6-diamino-4(3H)-oxopyrimidine-5yl)thio]propyl)thiophene-2-carboxylic acid:

NMR(DMSO-d6) δ=12.86(1H, broad), 10.02(1H, broad), 7.53(1H, d, J=3.7 Hz), 6.89(1H, d, J=3.7 Hz), 6.30(4H, br, s), 2.95(2H, t, J=7.4 Hz), 2.46(2H, t, J=6.9 Hz), (1.73 (2H, tt, J=6.9, 7.4 Hz); Anal. (C$_{12}$H$_{14}$N$_4$O$_3$S$_2$.0.5H$_2$O) C,H,N,S j) N-Diethyl N-[2-(5-[3-([2,6-diamino-4(3H)-oxopyrimidin-5-yl]thio]propyl)thienoyl)]-S-glutamate This product was prepared using the procedure described for example 2(i). From 1.31 grams (4 mmol) of 5-(3-[(2,6-diamino-4(3H)-oxopyriidin-5-yl)thio]propyl)thiophene-2-carboxylic there was obtained 879 mg (43% yield) of diethyl N-[2-(5-[3-([2,6-diamino-4(3H)-oxopyrimidin-5-yl]thio)propyl]thienoyl-S-glutamate as an off-white solid melting at 136–138° C.

The following analyses indicate that that product was diethyl N-[2-(5-[3-([2,6-diamino-4(3H )-oxopyrinidine-5-yl [thio)propyl]thienoyl)]-5-glutamate.

NMR (CDCl$_3$) δ=11.24 (1H, brs) 7.36 (1H, d, J=3.7 Hz), 7.02 (1H, d, J=7.8 Hz), 6.72 (1H, d, J=3.7 Hz), 6.29 (2H, broad), 5.55 (2H, broad), 4.72 (1H, ddd, J=4.8, 7.8, 12.6 Hz), 4.22 (2H, q, J=7.1 Hz), 4.10 (2H, q, J=7.1 Hz), 2.89 (2H, t, J=7.2 Hz), 2.55 (2H, t, J=7.0 Hz), 2.45 (2H, t, J=7.2 Hz), 2.34–2.22(1H, m), 2.18–2.08 (1H, m), 1.89 (2H, pentet, J=7.2 Hz), 1.29 (3H, t, J=7.1 Hz). Anal. (C$_{21}$H$_{29}$N$_5$O$_6$S$_2$) C,H,N,S k) N-[2-(5-[3-([2,6-diamino-4(3H)oxopyrimidin-5-yl]thio)propyl]thienoyl)]-S-glutamic acid This product was prepared using the procedure described for example 2(j). Saponification of 716 mg (1.4 mmol) of diethyl N-[2-(5-[3-([2,6-diamino-4(3H)-oxopyrimidin-5-yl]thio)propyl] thienoyl)]-S-glutamate yielded 558 mg (87% yield) of a yellow powder melting at 171 to 173° C.

The following analyses indicate that that product was N-[2-(5-[3-([2,6-diamino, 4(3H)-oxopyrimidine-5-yl]thio)-propyl] thionoyl)]-S-glutamic acid:

NMR(DMSO-d6) δ=12.41(2H, broad), 10.09(1H, broad), 8.49(1H, d, J=7.7 Hz), 7.66(1H, d, J=3.6 Hz), 6.85(1H, d, J=3.6 Hz), 6.39(4H, broad), 4.36–4.28(1H, m), 2,92(2H, t, J=7.2 Hz), 2.46(2H, t, J=6.8 Hz), 2.32(2H, t, J=7.3 Hz), 2.11–2.00(1H, m), 1.95–1.83(1H, m), 1.73(2H, tt, J=6.8, 7.2 Hz) Anal. ($C_{17}H_{21}N_5O_6S_2 \cdot 0.3H_2O$) C,H,N,S

EXAMPLE 4

Synthesis of N-[(4-[2-([2,6-diamino-4(3H)-oxopyrimidin-5-yl]thio)ethyl]thio)benzoyl]-S-glutamic acid This compound of formula III, wherein A is sulfur, n=2, x=S, Ar=1,4-phenylene-, and $R_1$ and $R_2$=H, was synthesized via the following process.

a) 4-[2[(t-butyldimethylsilyloxy)ethyl]thio]benzoic acid and methyl 4-[(2-hydroxyethyl)thio)benzoate A solution of 4-mercaptobenzoic acid (5.09 g, 33 mmol) in DMF (60 ml) was added to a slurry of 60% NaOH (2.64 g, 66 mmol) in DMF (60 ml) under argon at 0° C. This mixture was stirred at 0° C. for 90 minutes prior to the dropwise addition of a solution of 1-(tert.-butyldimethylsilyloxy)-2-iodoethane (8.59 g, 30 mmol) in DMF (30 ml). The resultant reaction mixture was stirred for 3 hours at room temperature, then poured over a mixture of 0.5N HCl (70 ml) and ice (200 g) and diluted with water (500 ml). The precipitate that formed was collected by filtration to give a peach-colored solid (9.28 g, 99% yield) which was used without further purification.

The above product 4-[2[(t-butyldimethylsilyloxy)-ethyl]thio] benzoic acid (8.75 g, 28 mmol) was dissolved in $CH_3OH$ (300 ml) containing conc. $H_2SO_4$ (3 ml) and this solution was refluxed overnight. The solvent was removed by concentration, in vacuo, and the residue was partitioned between saturated $NaHCO_3$ (300 ml) and ether (300 ml). The layers were separated and the aqueous phase extracted with EtOAc (200 ml). The combined organic extracts were dried over $Na_2SO_4$ and concentrated, in vacuo, to give an orange gum which was purified by flash chromatography. Elution with hexane/EtOAc (2:1) yielded the product as a white solid (3.53 g, 59% yield) which melted at 58° C.

The following analyses indicate that that product was methyl 4-(2-hydroxyethyl)thio benzoate:

NMR($CDCL_3$) δ=7.94(2H, d, J=8.5 Hz), 7.36(2H, d, J=8.5 Hz), 3.90(3H, s), 3.83(2H, q, J=6.1 Hz), 3.21 (2H, t, J=6.1 Hz), 1.96(1H, t, J=6.1 Hz); Anal. ($C_{10}H_{12}O_3S$) C,H,S b) Methyl 4-[(2-bromoethyl)thio]benzoate This product was prepared according to the procedure as described for example 2(d). From 1.06 grams (5 mmol) of methyl 4-[(2-hydroxyethyl)thio]benzoate, there was obtained 1.34 grams (97% yield) of a white solid melting at 77–78° C.

The following analyses indicate that that product was methyl 4-[(2-bromethyl)thio]benzoate:

NMR($CDCl_3$) δ=7.97(2H, d, J=8.5 Hz), 7.35(2H, d, J=8.5 Hz), 3.91(3H, s), 3.53–3.46(2H, m), 3.42–3.36(2H, m); Anal. ($C_{10}H_{11}O_2SBr$) C,H,S,Br c) Methyl 4-([2-(acetylthio)ethyl]thio)benzoate This product was prepared according to the procedure described for example 2(e). From 1.24 grams (45 mmol) of methyl 4-[(2-bromoethyl)thio]benzoate there was obtained 1.17 g (96% yield) of a yellow solid melting at 62–63° C.

The following analyses indicates that the product was methyl 4-([2-(acetylthio)ethyl]thio)benzoate:

NMR($CDCl_3$) δ=7.96(2H, d, J=8.6 Hz), 7.39(2H, d, J=8.6 Hz), 3.90(3H, s), 3.19–3.09(4H, m), 2.36(3H, s) Anal. ($C_{12}H_{14}O_3O_3S_2$) C,H,S d) Methyl 4-[(2-mercaptoethyl)thio]benzoate This product was prepared according to the procedure described for example 2(f). From 2.35 grams (8.7 mmol) of methyl-4-([2-(acetylthio)ethyl]thio)benzoate there was obtained 1.92 grams (97% yield) of a yellow solid melting at 51° C.

The following analyses indicate that that product was methyl 4-[(2-mercaptoethyl)thio]benzoate:

NMR ($CDCl_3$) δ=7.94(2H, d, J=8.5 Hz), 7.32(2H, d, J=8.5 Hz), 3.90(3H, s), 3.22(2H,t, J=7.2 Hz), 2.79 (2H, dt, J=8.3, 7.2 Hz), 1.73 (1H, t, J=8.3 Hz) Anal. ($CH_{10}H_{12}O_2S_2$) C,H,S e) Methyl 4-[(2-[(2,6-diamino-4(3H)-oxopyrimidin-5-yl)thio]ethyl)thio]benzoate This product was prepared according to the procedure described for example 2(g). From 2.51 grams (11 mmol) of methyl-4-([2-acetylthio)ethyl]thio)benzoate there was obtained 1.96 grams (56% yield) of a white solid melting at 219–221° C.

The following analysis indicate that that product was methyl 4-[(2-[(2,6-diamino-4(3H)-oxopyrimidin-5-yl)thio]ethyl) thio]benzoate:

NMR(DMSO-d6) δ=10.08(1H, br, s), 7.81(2H, d, J=8.5 Hz), 7.29(2H, d, J=8.5 Hz), 6.39(4H, broad), 3.82(3H, s), 3.16(2H, t, J=7.9 Hz), 2.66(2H, t, J=7.9 Hz); Anal. ($C_{14}H_{16}N_4O_3S_2 \cdot 0.9H_2O$) C,H,N,S f) 4-[(2-[(2,6-diamino-4(3H)-oxopyrimidin-5yl) thio]ethyl) thio]benzoic acid This product was prepared using the procedure described for example 2(h). Saponification of 1.76 grams (5 mmol) of methyl4-[(2-[(2,6-diamino-4(3H)oxopyrimidin-5-yl)thio]ethyl)thio]benzoate yielded 1.57 grams (93% yield) of a white solid melting at 273–275° C. (decomposed).

The following analyses indicate that that product was 4-[(2-[(2,6-diamino-4(3H)-oxopyrimidin-5yl) thio]ethyl) thio]benzoic acid:

NMR(DMSO-d6) δ=10.11(1H, br, s), 7.79(2H, d, J=8.5 Hz), 7.26(2H, d, J=8.5 Hz), 6.40(4H, broad), 3.15(2H, t, J=7.8 Hz), 2.66(2H, t, J=7.8 Hz); Anal. ($C_{13}H_{14}N_4O_3S_2$) C,H,N,S g) Diethyl N-[(4-[2-([2,6-diamino-4(3H)-oxopyrimidin-5yl]thio)ethyl]thio)benzoyl]-S-glutamate This product was prepared using the procedure described for example 2 (i). From 1.36 grams (4 mmol) of 4-[(2-[(2, 6-diamino(3H)-oxopyrimidin-5-yl)thio]ethyl)thio] benzoic acid there was obtained 905 mg (43% yield) of an off-white solid melting at 87 to 89° C.

The following analyses indicate that that product was diethyl N-[(4-[2-([2,6-diamino-4(3H)-oxopyrimidin-5yl]thio)ethyl]thio)benzoyl]-S-glutamate:

NMR($CDCl_3$) δ=11.18(1H, br, s), 7.65(2H, d, J=8.4 Hz), 7.38(1H, d, J=7.9 Hz), 7.22(2H, d, J=8.4 Hz), 6.54(2H, broad), 5.67(2H, broad), 4.77 (1H, ddd, J=4.8, 7.9, 12.7 Hz), 4.21(2H, q, J=7.1 Hz), 4.08(2H, q, J=7.1 Hz), 3.10(2H, t, J=7.5 Hz), 2.70(2H, t, J=7.5 Hz), 2.62–2.40(2H, m), 2.37–2.24(1H, m), 2.21–2.09(1H, m), 1.29(3H, t, J=7.1 Hz), 1.21(3H, t, J=7.1 Hz); Anal. ($C_{22}H_{29}N_5O_6S_2$) C,H,N,S h) N-[(4-[2-([2,6-diamino-4(3H)-oxopyrimidin-5-yl]thio) ethyl]thio)benzoyl-S-glutamic acid This product was prepared using the procedure described for example 2 (j). From 649 mg (1.2 mmol) of the corresponding diethyl ester, there was obtained 529 mg (91% yield) of a white solid melting at 161–162° C. (dec.).

The following analyses indicate that that product was N-[(4-[2-([2,6-diamino-4(3H)-oxopyrimidin-5-yl]thio) ethyl]thio)benzoyl]-S-glutamic acid:

NMR(DMSO-d6) δ=12.39(2H, broad), 10.22(1H, broad), 8.58(1H, d, J=7.7 Hz), 7.78(2H, d, J=8.4 Hz), 7.28(2H, d, J=8.4 Hz), 6.56(2 H, broad), 6.44(2H, broad), 4.37(1H, ddd, J=4.9, 7.7, 12.6 Hz), 3.14(2H, t, J=7.8 Hz), 2.66(2H, t, J=7.8 Hz), 2.34(2H, t, J=7.4 Hz), 2.13–2.03 (1H, m), 2.01–1.87 (1H, m)); Anal. ($C_{18}H_{21}N_5O_6S_2$.1.8HCl) C,H,N,S

EXAMPLE 5

Synthesis of N-[4-(N-[2-([2,6-diamino-4(3H)-oxopyrimidin-5-yl]thio)ethyl]amino)benzoyl]-S-glutamic acid This compound of formula III, wherein A is sulfur, n=2, x=—NH—, Ar=1,4-phenylene-, and $R_1$ and $R_2$=H, was synthesized via the following process.

(a) methyl 4-(N-[2-(tert.-butyldimethylsilyloxy)ethyl] amino) benzoate

To a solution of 1-(tert.-butyldimethylsilyloxy)-2-iodoethane (45.10 gm, 160 mmol) in DMF (50 mL) was added methyl 4-aminobenzoate (4.54 gm, 30 mmol) and diisopropylethylamine (6 mL, 34 mmol). This solution was heated at 95° for approximately 21 hours. The solvent was removed by concentration, in vacuo, and the residue obtained was partitioned between $CH_2Cl_2$ (150 mL) and water (150 mL). The layers were separated and the aqueous phase extracted with $CH_2Cl_2$ (150 mL). The combined organic extracts were washed with 10% $Na_2S_2O_3$ (120 mL), dried over $Na_2SO_4$ and concentrated, in vacuo, to give an orange oil which was purified by flash chromatography. Elution with hexane: EtOAc (9:1) provided the product as a colorless oil (3.85 gm, 41% yield).

The following analyses indicated that the product was methyl 4-(N-[2-(tert.-butyldimethylsilyloxy)ethyl]-amino) benzoate:

NMR(CDCL$_3$) δ=7.86(2H, d, J=8.8 Hz), 6.57(2H, d, J=8.8 Hz), 4.48(1H, broad), 3.85(3H, s), 3.82(2H, t, J=5.2 Hz), 3.27(2H, q, J=5.2 Hz), 0.90(9H, s), 0.06(6H, s); Anal. ($C_{16}H_{27}NO_3Si$) C,H,N (b) methyl 4-[N-(2-hydroxyethyl)amino]benzoate A 1.0M solution of tetrabutylammonium fluoride in THF (30 mL, 30 mmol) was added to a solution of methyl 4-(N-[2-(tert.-butyldimethylsilyloxy)ethyl]amino)benzoate (3.67 gm, 12 mmol) in THF (50 mL). This mixture was stirred for 18 hours at ambient temperature, then diluted with water (100 mL) and extracted with ether (2×75 mL) and EtOAc (75 mL). The combined organic extracts were washed with brine (90 mL), dried over $Na_2SO_4$ and concentrated, in vacuo, to give a yellow gum which was purified by flash chromatography. Elution with hexane: EtOAc (1:1) yielded 2.10 gm (91%) of product as a white solid melting at 116° to 117°.

The following analyses indicated that the product was methyl 4-[N-(2-hydroxyethyl)amino]benzoate:

NMR(CDCL$_3$) δ=7.85(2H, d, J=8.8 Hz), 6.58(2H, d, J=8.8 Hz), 4.52(1H, broad), 3.89–3.83(5H, m), 3.34(2H, q, J=5.2 Hz), 1.98(1H, t, J=5.1 Hz); Anal. ($C_{10}H_{13}NO_3$) C,H,N (c) methyl 4-(N-[2-(acetylthio)ethyl]amino)benzoate A solution of triphenylphosphine (7.34 gm, 28 mmole) in THF (60 mL) was cooled to 0°. Diethyl azidodicarboxylate (4.4 mL, 28 mmol) was added to this solution which was stirred at 0° for 30 minutes. To this mixture was added a solution of methyl 4-[N-(2-hydroxyethyl)amino)benzoate (2.73 gm, 14 mmol) and thio]acetic acid (2.0 mL, 28 mmol) in THF (30 mL). The resultant mixture was stirred at 0° for 45 minutes, then for an additional 2 hours at ambient temperature. The solvent was then removed by concentration, in vacuo, and the residue obtained was purified by flash chromatography. Elution with hexane: EtOAc (4:1) yielded 1.87 gm (53%) of product as a white solid melting at 90° to 91°.

The following analyses indicated that the product was methyl 4-(N-[2-(acetylthio)ethyl]amino)benzoate:

NNR (CDCL$_3$) δ=7.86(2H, d, J=8.8 Hz), 6.58(2H, d, J=8.8 Hz), 4.47(1H, t, J=6.5 Hz), 3.84(3H, s), 3.39(2H, q, J=6.5 Hz), 3.10(2H, t, J=6.5 Hz), 2.37(3H, s); Anal. ($C_{12}H_{15}NO_3S$) C,H,N,S (d) methyl 4-[N-(2-thioethyl)amino]benzoate To a solution of methyl 4-(N-[2-(acetylthio)ethyl]amino)-benzoate (1.95 gm, 7.7 mmol) in methanol (40 mL) was added 15 mL of 2N NaCl. This mixture was heated at reflux for 16 hours, then diluted with saturated $NaHCO_3$ (75 mL) and ether (75 mL). The layers were separated and the aqueous phase was extracted with ether (2×60 mL). The combined organic extracts were dried over $Na_2SO_4$ and concentrated, in vacuo, to give a colorless oil which was purified by flash chromatography. Elution with $CH_2Cl_2$: hexane (4:1) yielded 1.17 gm (72%) of product as a white solid melting at 46° to 47°

The following analyses indicated that the product was methyl 4-[N-2(-thioethyl)amino]benzoate:

NMR(CDCL$_3$) δ=7.87(2H, d, J=8.8 Hz), 6.59(2H, d, J=8.8 Hz), 3.85(3H, s),3.41(2H, t, J=6.4 Hz), 2.78(2H, dt, J=8.3, 6.4 Hz), 1.42(1H, t, J=8.3 Hz); Anal. ($C_{10}H_{13}NO_2S$) C,H,N,S (e) methyl 4-[N-(2-[(2,6-diamino-4(3H)-oxopyrimidin-5-yl) thio]ethyl)amino]benzoate This material was prepared using the procedure described in example 2(g). From 1.96 gm (9.3 mmol) of methyl 4-[N-(2-thioethyl)amino] benzoate there were obtained 916 mg (29%) of a beige solid melting at 253° (dec.)

The following analyses indicated that the product was methyl 4-[N-(2-[(2,6-diamiono-4(3H)-oxopyrimidin-5-yl) thio]ethyl)amino]benzoate:

NMR(DMSO-d6) δ=10.11(1H, s), 7.66(2H, d, J=8.7 Hz), 6.55(2H, d, J=8.7 Hz), 6.43(2H, broad), 6.36(2H, br s), 3.72(3H, s), 3.16(2H, t, J=6.4 Hz), 2.59(2H, t, J=6.4 Hz); Anal. ($C_{14}H_{17}N_5O_3S$.0.1H1O.0.6H$_3$OH) C,H,N,S (f) 4-[N-(2-[2,6-diamino-4(3H)-oxopyrimidin-5-yl)thio] ethyl)amino]benzoic acid This material was prepared using the procedure described in example 2(h). From 838 mg (2.5 mmol) of methyl 4-[N-(2[2,6-diamino-4(3H)-oxopyrimidin-5-yl)thio]ethyl) amino]benzoate there were obtained 786 mg (98%) of an off-white solid melting at 263° (dec.)

The following analyses indicated that the product was 4-[N-(2-[(2,6-diamino-4(3H)-oxopyrimidin-5-yl)thio]ethyl) amino]-benzoic acid:

NMR(DMSO-d6) δ=11.34(1H, broad), 7.93(2H, broad), 7.65(2H, d, J=8.7 Hz), 7.31(2H, broad), 6.55(2H, d, J=8.7 Hz), 3.20(2H, t, J=6.7 Hz), 2.65(2H, t, J=6.7 Hz); Anal. ($C_{13}H_{15}N_5O_3S$.1.1 HCl) C,H,N,S (g) diethyl N-[4-(N-[2-([diamino-4(3H)-oxopyrimidin-5-yl] thio)ethyl]amino benzoyl]-S-glutamate This material was prepared using the procedure described for example 2(i). From 707 mg (2.2 mol) of 4-[N-(2-[(2,6-diamino-4(3H)-oxopyrimidin-5-yl)thio]ethyl)amino] benzoic acid there were obtained 215 mg (19%) of a white solid melting at 173°–174°

The following analyses indicated that the product was diethyl N-[4-(N-[2-([2-([2,6-diamino-4(3H)-oxopyrimidin-5-yl]thio)ethyl]amino)benzoyl]-S-glutamate:

NMR(DMSO-d6) δ=10.11(1H, s), 8.23(1H, d, J=7.3 Hz), 7.63(2H, d, J=8.6 Hz), 7.08(1H, broad), 6.54(2H, d, J=8.6 Hz), 6.42(2H, br s), 6.36(2H, br s), 4.35(1H, ddd, J=5.6, 7.3, 12.8 Hz), 4.07(2H, q, J=7.0 Hz), 4.03(2H, q, J=7.0 Hz),3.16 (2H, t, J=6.4 Hz), 2.59(2H, t, J=6.4 Hz), 2.40(2H, t, J=7.4 Hz), 2.09–1.91(2H, m), 1.17(3H, t, J=7.0 Hz), 1.15(3H, t, J=7.0 Hz); Anal. ($C_{22}H_{30}N_6O_6S$.0.6 CH$_3$OH) C,H,N,S (h) N-[4-(N-[2-([2,6-diamino-4(3H)-oxopyrimidin-5-yl)thio]ethyl]amino)benzoyl]-S-glutamic acid This material was prepared using the procedure described for example 2(j). From 175 mg (0.35 mmol) of diethyl N-[4-(N-[2-([2,6-diamino-4(3H)-oxopyrimidin-5-yl]thio)ethyl]amino)-benzoyl]-S-glutamate there were obtained 115 mg (75%) of a white solid melting at 227到 to 228° (dec.)

The following analyses indicated that the product was N-[4-(N-[2-([2,6-diamino-4(3H)-oxopyrimidin-5-yl]thio)ethyl]amino)benzoyl]-S-glutamic acid:

NMR(DMSO-d6) δ=12.25(2H, broad), 10.09(1H, broad), 8.09(1H, d, J=7.7 Hz), 7.61(2H, d, J=8.6 Hz), 6.51(2H, d, J=8.6 Hz), 6.42(2H, br s), 6.35(2H, br 8), 4.30(1H, ddd, J=5.3, 7.7, 12.6 Hz), 3.13(2H, t, J=6.4 Hz), 2.56(2H, t, J=6.4 Hz), 2.29(2H, t, J=7.3 Hz), 2.05–1.95(1H, m), 1.93–1.83 (1H, m); Anal. ($c_{18}H_{22}N_6O_6S$) C,H,N,S

EXAMPLE 6

N-[5-(3-[2,6-Diamino-4(3H)-oxopyrimidin-5-yl)thio]propyl)-3-methyl-thieno-2-yl]-L-glutamic acid (a) 2-[(5-Bromo-3-methyl-thiophene-2-carbonyl)-amino]-glutamic acid diethyl ester

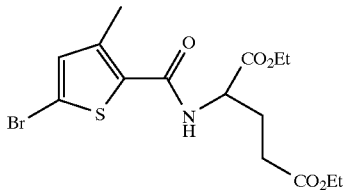

To a stirred solution of 10.86 g (49.1 mmol) of 5-Bromo-3-methyl-thiophene-2-carboxylic acid (prepared according to D. Spinelli, JCS Perkin Trans. II, 1972, 1866), 6.97 g (51.6 mmol) of 1-Hydroxybenzotriazole hydrate, 9.0 mL (51.7 mmol) of diisopropylethylamine and 12.36 g (51.6 mmol) of L-glutamic acid diethyl ester hydrochloride in 70 mL of DMF was added 9.89 g (51.6 mmol) of 1-(3-Dimethylaminopropyl)-3-ethyl-carbodiimide hydrochloride. The reaction mixture was stirred under Argon for 18 hours, poured into $H_2O$ and extracted with ethyl acetate. The organic layer was washed sequentially with 0.5 N HCl, saturated $NaHCO_3$ soln and saturated NaCl soln, dried over $MgSO_4$, then concentrated under reduced pressure. This residue was purified by flash chromatography on silica gel eluting methylene chloride-ethyl acetate (20:1). In this manner, there was obtained 19.70 g (99%) of the desired product as a colorless oil.

IR (neat) 3329, 2982, 1738, 1651,1545, 1514, 1417, 1377, 1258, 1206 cm$^{-1}$. 'H NMR (CDCl$_3$) δ 1.24 (3H, t, J=7.1 Hz), 1.30 (3H, t, J=7.1 Hz), 2.04–2.45 (4H, m), 2.48 (3H, s), 4.12 (2H, q, J=7.1 Hz), 4.23 (2H, q, J=7.1 Hz), 4.71 (1H, ddd, J=12.3, 7.2, 4.8 Hz), 6.56 (1H, d, J=7.3 Hz), 6.87 (1H, s). Anal. (calc. for $C_{15}H_{20}BrNO_5S$); C, H, Br, N, S.

(b) 2-{[5-(3-Hydroxy-prop-1-ynyl]-3-methyl-thio-phene-2-carbonyl]-amino}-glutamic acid diethyl ester

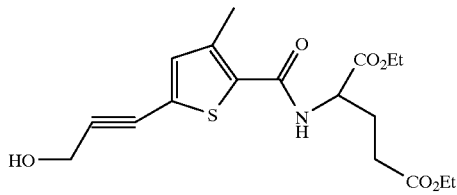

To a stirred solution of 13.73 g (33.8 mmol) of bromide 6(a) and 2.36 mL (40.5 mmol) of propargyl alcohol in 170 mL of diethylamine was added 0.47 g (0.7 mmol) of bis(triphenylphosphine) palladium (II) chloride and 0.13 g (0.7 mmol) of cuprous iodide. The reaction mixture was stirred under Argon for 18 hours. The volatiles were evaporated under reduced pressure and the brown residue was purified by flash chromatography on silica gel eluting methylene chloride-ethyl acetate (9:1). In this manner, there was obtained 12.36 g (96%) of the desired product as a yellow oil.

IR (neat) 3366, 2982, 2250, 1738, 1640, 1545, 1516, 1445, 1377 cm$^{-1}$. 'H NMR (CDCl$_3$) δ 1.24 (3H, t, J=7.1 Hz), 1.30 (3H, t, J=7.1 Hz), 1.80 (1H, broad t), 2.04–2.46 (4H, m), 2.47 (3H, s), 4.12 (2H, q, J=7.0 Hz), 4.24 (2H, q, J=7.1 Hz), 4.50 (2H, d, J=5.2 Hz), 4.73 (1H, m), 6.63 (1H, d, J=7.3 Hz), 6.96 (1H, s). Anal. (calc. for $C_{18}H_{23}NO_6S$); C, H, N, S.

(c) 2-{[5-(3-Hydroxy-propyl)-3-methyl-thio-phene-2-carbonyl]-amino}-glutamic acid diethyl ester

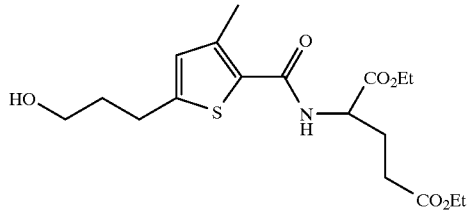

A Parr flask containing 10.32 g (27.1 mmol) of alkyne 6(b), 4.00 g of 5% Pd/C and 150 mL of ethanol was shaken under 45 psi of hydrogen for 2 hours. The reaction mixture was filtered through a pad of Celite and the filtrate was concentrated under reduced pressure. In this manner, there was obtained 9.80 g (94%) of the desired product as a colorless oil.

IR (neat) 3354, 2980, 2930, 1732, 1634, 1514, 1447, 1377 cm$^{-1}$. 'H NMR (CDCl$_3$) δ 1.23 (3H, t, J=7.1 Hz), 1.30 (3H, t, J=7.1 Hz), 1.93 (2H, pentet, J=7.2 Hz), 2.08–2.46 (4H, m), 2.47 (3H, s), 2.88 (2H, t, J=7.6 Hz), 3.70 (2H, t, J=6.3 Hz), 4.11 (2H, q, J=7.1 Hz), 4.23 (2H, q, J=7.1 Hz), 4.75 (1H, m), 6.47 (1H, d, J=7.3 Hz), 6.62 (1H, s). Anal. (calc. for $C_{18}H_{27}NO_6S$); C, H, N, S.

(d) 2-{[5-(3-Acetylsulfanyl-propyl)-3-methyl-thio-phene-2-carbonyl]-amino}-glutamic acid diethyl ester

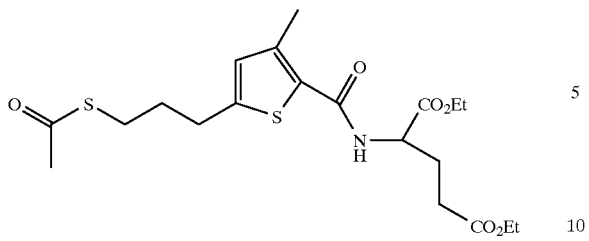

This material was prepared according to the procedure described in example 5(c) using alcohol 6(c). The product (67%) was isolated as a yellow oil by flash chromatography on silica gel eluting methylene chloride-ethyl acetate (20:1).

IR (neat) 3366, 2980, 2936, 1736, 1692, 1649, 1510, 1447, 1377 cm$^{-1}$. $^1$H NMR (CDCl$_3$) δ 1.23 (3H, t, J=7.2 Hz), 1.30 (3H, t, J=7.1 Hz), 1.95 (2H, pentet, 7.3 Hz), 2.04–2.48 (4H, m), 2.34 (3H, s), 2.47 (3H, s), 2.83 (2H, t, J=7.4 Hz), 2.91 (2H, t, J=7.2 Hz), 4.11 (2H, q, J=7.1 Hz), 4.23 (2H, q, J=7.1 Hz), 4.75 (1H, m), 6.47 (1H, d, J=7.4 Hz), 6.61 (1H, s).

(e) N-[5-(3-[(2,6-Diamino-4(3H)-oxopyrimidin-5.yl) thio] propyl)-3-methyl-thieno-2-yl]-L-glutamic acid diethyl ester

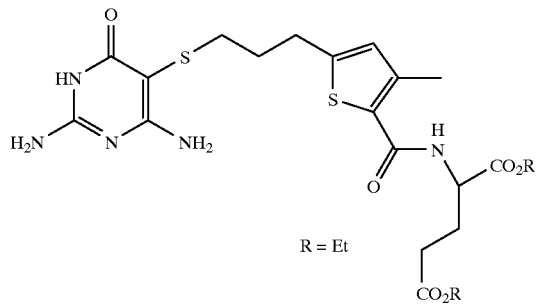

A stirred solution of 0.40 g (0.90 mmol) of thioacetate 6(d) in 10 mL of ethanol saturated with dry HCl gas was heated at 50° C. under Argon for 2 hours. The volatiles were removed under reduced pressure. The residue was dissolved in methylene chloride and re-concentrated to remove traces of HCl. This procedure was repeated twice. The resulting crude thiol and 0.18 g (0.90 mmol) of 5-Bromo-2,6-diamino-4(3H) pyrimidinone were dissolved in degassed DMF. To this solution was added 0.15 mL (0.90 mmol) of diisopropyl-ethylamine. After heating under Argon at 100° C. for 2.5 hours, the cooled reaction mixture was poured into H$_2$O and extracted with ethyl acetate. The organic layer was washed twice with sat. NaCl soln, dried over MgSO$_4$ and concentrated at reduced pressure. The residue was flash chromatographed on silica gel eluting methylene chloride-methanol (9:1). In this manner, there was obtained 0.17 g (38%) of the desired product as a white solid.

mp 164–165° C. IR (KBr) 3329, 2930, 1734, 1636, 1597, 1518, 1441 cm$^{-1}$. $^1$H NMR (dmso-d$_6$) δ 1.16 (3H, t, J=7.1 Hz), 1.18 (3H, t, J=7.0 Hz), 1.71 (2H, m), 1.90–2.10 (2H, m), 2.32 (3H, s) 2.40 (4H, m), 2.86 (2H, t, J=7.4 Hz), 4.07 (4H, m), 4.32 (1H, m), 6.30 (4H, broad s), 6.67 (1H, s), 8.13 (1H, d, J=7.5 Hz), 9.95 (1H, s) Anal. (calc. for C$_{22}$H$_{31}$N$_5$O$_6$S$_2$.1.0 H$_2$O); C, H, N, S.

(f) N-[5-(3-[2,6-Diamino-4(3H)-oxopyrimidin-5-yl)thio] propyl)-3-methyl-thieno-2-yl]-L-glutamic acid

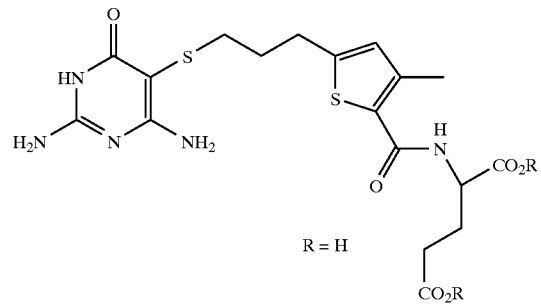

R = H

This product was prepared according to the general procedure described in example 2(j) using diethyl ester 6(e). The product (82%) was collected as a white solid:

mp 217–220° C. IR (KBr) 3341, 3200, 2922, 1709, 1620, 1516, 1468, 1263 cm$^{-1}$. $^1$H NMR (dmso-d$_6$) δ 1.71 (2H, pentet, J=7.2 Hz), 1.74–2.05 (2H, m), 2.31 (2H, t, J=7.5 Hz), 2.33 (3H, s), 2.46 (2H, t, J=6.9 Hz), 2.86 (2H, t, J=6.9 Hz), 4.28 (1H, m), 6.33 (4H, broad 9), 6.66 (1H, s), 7.96 (1H, d, J=7.7 Hz), 9.96 (1H, broad s). Anal. (calc. for C$_{18}$H$_{23}$N$_5$O$_6$S$_2$.1.3 H$_2$O); C, H, N, S.

EXAMPLE 7

N-[5-(3-[2,6-Diamino-4(3H)-oxopyrimidin-5-yl) thio]propyl)-4-methyl-thieno-2-yl}-L-glutamic acid (a) 2-[(5-Bromo-4-methyl-thiophene-2-carbonyl)-amino]-glutamic acid diethyl ester

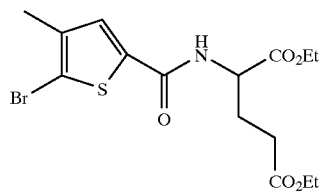

The starting 5-Bromo-4-methyl-thiophene-2-carboxylic acid was prepared according to M. Nemec, Collection Czechoslav. Chem. Commun. 39, 3527, (1974).

The titled compound was prepared according to the general procedure described in example 6(a) and isolated (89%) as a lt. yellow oil by flash chromatography on silica gel eluting methylene chloride-ethyl acetate (25:1).

IR(neat) 3339, 2984, 1738, 1634, 1562, 1527, 1425, 1209 cm$^{-1}$. $^1$H NMR (CDCl$_3$) δ 1.24 (3H, t, J=7.1 Hz), 1.30 (3H, t, J=7.1 Hz), 2.04–2.52 (4H, m), 2.20 (3H, s), 4.12 (2H, q, J=7.3 Hz), 4.23 (2H, q, J=7.3 Hz), 4.70 (1H, ddd, J=12.3, 7.7, 4.8 Hz), 6.84 (1H, d, J=7.4 Hz), 7.22 (1H, s). Anal. (calc. for C$_{15}$H$_{20}$BrNO$_5$S); C, H, Br, N, S.

(b) 2-{[5-(3-Hydroxy-prop-1-ynyl)-4-methyl-thiophene-2-carbonyl]-amino}-glutamic acid diethyl ester

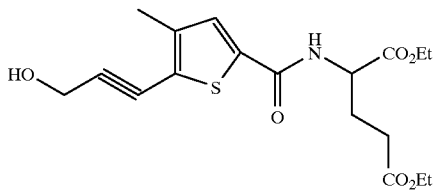

This material was prepared according to the general procedure described in example 6(b) using the bromo compound 7(a). The product (94%) was isolated as a lt. yellow oil by flash chromatography on silica gel eluting a gradient of 8–11% ethyl acetate in methylene chloride.

IR(neat) 3329, 2980, 2222, 1738, 1634, 1557, 1532, 1447 cm$^{-1}$. 'H NMR (CDCl$_3$) δ 1.23 (3H, t, J=7.1 Hz), 1.29 (3H, t, J=7.2 Hz), 2.04 (3H, s), 2.07–2.50 (4H, m), 4.14 (2H, q, J=7.1 Hz), 4.24 (2H, q, J=7.1 Hz), 4.54 (2H, s), 4.71 (1H, m), 6.88 (1H, d, J=7.4 Hz), 7.27 (1H, s). Anal. (calc. for C$_{18}$H$_{23}$NO$_6$S); C, H, N, S.

(c) 2-{[5-(3-Hydroxy-propyl)-4-methyl-thiophene-2-carbonyl]-amino}-glutamic acid diethyl ester

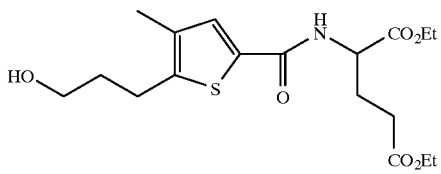

This material was prepared according to the general procedure described in example 6(c) using alkyne 7(b). The product (100%) was isolated as a colorless oil.

IR (neat) 3337, 2980, 2938, 1738, 1632, 1560, 1530, 1449 cm$^{-1}$. 'H NMR (CDCl$_3$) δ 1.23 (3H, t, J=7.2 Hz), 1.30 (3H, t, J=7.1 Hz), 1.89 ((2H, pentet, J=7.2 Hz), 2.06–2.49 (4H, m) 2.16 (3H, s), 2.85 (2H, t, J=7.5 Hz), 3.70 (2H, t, J=6.3 Hz), 4.11 (2H, q, J=7.1 Hz), 4.23 (2H, q, J=7.2 Hz), 4.74 (1H, m), 6.67 (1H, d, J=7.6 Hz), 7.26 (1H, s). Anal. (calc. for C$_{18}$H$_{27}$NO$_6$S); C, H, N, S.

(d) 2-{[5-(3-Acetylsulfanyl-propyl)-4-methyl-thiophene-2-carbonyl]-amino}-glutamic acid diethyl ester

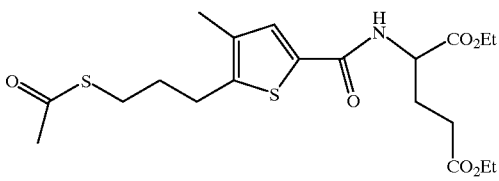

This material was prepared according to the general procedure described in example 5(c) using alcohol 7(c). The product (56%) was isolated as a yellow oil by flash chromatography on silica gel eluting ether-hexanes (2:1).

IR (neat) 3337, 2982, 2938, 1736, 1694, 1634, 1526, 1449, 1206 cm$^{-1}$. 'H NMR (CDCl$_3$) δ 1.20 (3H, t, J=7.1 Hz), 1.30 (3H, t, J=7.1 Hz), 1.91 (2H, pentet, J=7.4 Hz), 2.08–2.49 (4H, m), 2.15 (3H, s), 2.34 (3H, s), 2.80 (2H, t, J=7.4 Hz), 2.91 (2H, t, J=7.2 Hz), 4.13 (2H, q, J=7.1 Hz), 4.24 (2H, q, J=7.2 Hz), 4.74 (1H, m), 6.67 (1H, d, J=7.6 Hz), 7.26 (1H, s). Anal. (calc. for C$_{20}$H$_{29}$NO$_6$S$_2$); C, H, N, S.

(e) N-[5-(3-[(2,6-Diamino-4(3H)-oxopyrimidin-5-yl)thio] propyl)-4-methyl-thieno-2-yl]-L-glutamic acid diethyl ester

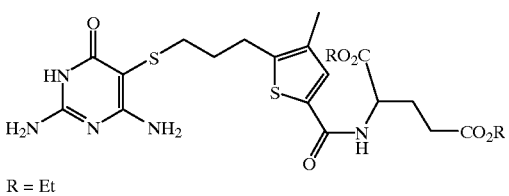

R = Et

This material was prepared according to the general procedure described in example 6(e) using thio acetate 7(d). The product (48%) was isolated as a white solid by flash chromatography eluting methylene chloride-methanol (9:1).

mp 159–160° C. IR (KBr) 3324, 2980, 1734, 1657, 1632, 1603, 1466, 1206 cm$^{-1}$. 'H NMR (dmso-d$_6$) δ 1.15 (3H, t, J=7.1 Hz), 1.17 (3H, t, J=7.1 Hz), 1.68 (2H, m), 2.01 (2H, m), 2.11 (3H, s), 2.43 (4H, m), 2.85 (2H, t, J=7.3 Hz), 4.04 (2H, q, J=7.1 Hz), 4.12 (2H, q, J=7.1 Hz), 4.34 (1H, m), 6.31 (4H, broad s), 7.55 (1H, s), 8.52 (1H, d, J=7.5 Hz), 9.95 (1H, s). Anal. (calc. for C$_{24}$H$_{31}$N$_5$O$_6$S); C, H, N, S.

(f) N-[5-(3-[2,6-Diamino-4(3H)-oxopyrimidin-5-yl) thio] propyl)-4-methyl-thieno-2-yl]-L-glutamic acid

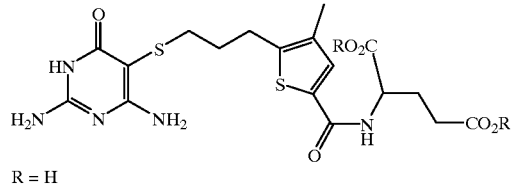

R = H

This product was prepared according to the general procedure described in example 2(j) using diethyl ester 7(e). The product (87%) was collected by filtration as a white solid.

mp 154–158° C. IR (KBr) 3322, 3179, 2922, 1705, 1632, 1564, 1445 cm$^{-1}$. 'H NMR (dmso-d$_6$) δ 1.68 (2H, m), 1.92–2.01 (2H, m), 2.10 (3H, s), 2.31 (2H, t, J=7.4 Hz), 2.47 (2H, t, J=7.4 Hz), 2.82 (2H, t, J=7.4 Hz), 4.29 (1H, m), 6.29 (4H, broad s), 7.53 (1H, s), 8.36 (1H, d, J=7.7 Hz), 9.90 (1H, broad Anal. (calc. for C$_{18}$H$_{23}$N$_5$O$_6$S$_2$.0.40H$_2$O); C, H, N, S.

EXAMPLE 8

Synthesis of N-(6-[([2,6-diamino-4(3H) oxopyrimidiro-5-yl]-thio)methyl]-4,5,6,7-tetrahydrobenzothieno-2-yl)-S-glutamic acid This compound of Formula II, wherein A=S, group=CH$_2$, ring=6,2-(4,5,6,7-tetrahydrobenzothienyl) and R$_1$, R$_2$ and R$_3$=H, was synthesized via the following process.

(a). bromomethyl 3-thienyl ketone

To a chilled solution of 3-acetylthiophene (12.62 g, 100 mmol) in THF (350 mL) was added phenyltrimethylammonium tribromide (39.10 g, 104 mmol). This mixture was left standing, with occasional swirling, for 2 hours at 0°. The precipitate was removed by filtration and washed with ether (2×75 mL). The combined filtrates were poured into a mixture of saturated NaHCO$_3$ (200 mL) and 10% Na$_2$S$_2$O$_3$ (200 mL). The layers were separated and the aqueous phase extracted with EtOAc (150 mL). The combined organic extracts were dried over Na$_2$SO$_4$ and concentrated, in vacuo, to give a brown oil which was purified by flash chromatography. Elution with hexane: CH$_2$Cl$_2$ (2:1) provided the product as a white solid (15.54 g, 76% yield) melting at 60°–61°.

The following analyses indicated that the product was bromomethyl 3-thienyl ketone.

NMR (CDCl$_3$) δ=8.18 (1H, dd, J=1.3, 2.9 Hz), 7.58 (1H, dd, J=1.3, 5.1 Hz), 7.37 (1H, dd, J=2.9, 5.1 Hz), 4.34 (2H, s); Anal. (C$_6$H$_5$OSBr) C, H, S, Br (b). diethyl 2-[2-oxo-2-(3-thienyl)ethyl] malonate Diethyl malonate (6.5 mL, 6.86 g, 42.8 mmol) was added dropwise to a suspension of sodium hydride (1.66 g, 41.5 mmol) in THF (15 mL) under argon at 0°. After stirring at 0° for 15 minutes, a solution of bromomethyl 3-thienyl ketone 8(a) (5.20 g, 25.4 mmol) in THF (60 mL) was added to this mixture. The resultant, yellow slurry was stirred at ambient temperature for 1 hour, then diluted with EtOAc (100 mL) and poured into water (150 mL). The layers were separated and the aqueous phase extracted with EtOAc (2×100 mL). The combined organic extracts were washed with brine (100 mL), dried over $MgSO_4$ and concentrated, in vacuo, to give a yellow oil which was purified by flash chromatography. Elution with hexane:EtOAc (5:1) provided the product as a pale yellow oil (5.63 g, 78%).

The following analyses indicated that the product was diethyl 2-[2-oxo-2-(3-thienyl)ethyl] malonate.

NMR ($CDCl_3$) δ=8.12 (1H, dd, J=1.2, 2.9 Hz), 7.55 (1H, dd, J=1.2, 5.1 Hz), 7.33 (1H, dd, J=2.9, 5.1 Hz), 4.23 (2H, q, J=7.1 Hz), 4.22 (2H, q, J=7.1 Hz), 4.04 (1H, t, J=7.2 Hz), 3.54 (2H, d, J=7.2 Hz), 1.29 (6H, t, J=7.1 Hz); Anal. ($C_{13}H_{16}O_5S$) C, H, S (c). 2-[2-oxo-2-(3-thienyl)ethyl] malonic acid Diethyl 2-[2-oxo-2-(3-thienyl) ethyl] malonate 8(b) (5.39 g, 19 mmol) was suspended in 10% KOH (50 mL) and left stirring at ambient temperature for 18 hours. The resultant solution was acidified to pH 1 by addition of 6N HCL and the precipitate that formed was collected by filtration to provide the product (4.22 g, 98%) as an off-white solid melting at 161°–162° (dec.).

The following analyses indicated that the product was 2-[2-oxo-2-(3-thienyl)ethyl] malonic acid.

NMR (DMSO-d6) δ=12.85 (2H, broad), 8.59 (1H, dd, J=1.2, 2.8 Hz), 7.62 (1H, dd, J=2.8, 5.1 Hz), 7.49 (1H, dd, J=1.2, 5.1 Hz), 3.75 (1H, t, J=7.2 Hz), 3.44 (2H, d, J=7.2 Hz);

(d). 4-(3-thienyl) butyric acid

Hydrazine hydrate (1.3 mL, 1.34 g, 26.8 mmol) was added dropwise to a solution of KOH (3.54 g, 63 mmol) and 2-[2-oxo-2-(3-thienyl) ethyl] malonic acid 8(c) (4.00 g, 17.5 mmol) in ethylene glycol (30 mL). This solution was heated at reflux for 6 hours. After cooling to room temperature, the crude reaction mixture was poured into a mixture of 6N HCl (50 mL) and ice (200 g). This aqueous mixture was saturated with NaCl, then extracted with ether (3×70 mL). The combined organic extracts were dried over $Na_2SO_4$ and concentrated, in vacuo, to provide an orange oil (2.61 g) of sufficient purity to be employed in the-subsequent reaction without any further purification.

(e). 7-oxo-4,5,6,7-tetrahydrobenzothiophene

To a solution (8% by wt) of $P_2O_5$ in methanesulfonic acid (80 mL) was added the crude 4(3-thienyl) butyric acid 8(d) (2.61 g, 15.3 mmol). The resultant reaction mixture was stirred at ambient temperature for 90 minutes, then cautiously poured into water (450 mL). After cooling to room temperature, this aqueous mixture was extracted with EtOAc (3×200 mL). The combined organic extracts were washed with saturated $NaHCO_3$ (2×150 mL) and brine (150 mL), dried over $MgSO_4$ and concentrated, in vacua, to give a brown oil which was purified by flash chromatography. Elution with hexane:EtOAc (4:1) provided the product as a yellow oil (1.65 g, 71%).

The following analyses indicated that the product was 7-oxo-4,5,6,7-tetrahydrobenzothiophene.

NMR ($CDCl_3$) δ=7.61 (1H, d, J=4.9 Hz), 6.97 (1H, d, J=4.9 Hz), 2.88 (2H, t, J=6.1 Hz), 2.61 (2H, t, J=6.5 Hz), 2.18 (2H, tt, J=6.5 Hz); Anal. ($C_8H_8OS$) C, H, S (f). methyl-7-oxo-4,5,6,7-tetrahydrobenzothiophene-6-carboxylate A solution of 7-oxo-4,5,6,7-tetrahydrobenzothiophene 8(e) (1.37 g, 9 mmol) in DMF (10 mL) was added dropwise, under an argon atmosphere, to a suspension of NaH (800 mg, 20 mmol) in DMF (6 mL). The resultant, purple solution was stirred at ambient temperature for 15 minutes, then cooled to 0° prior to the dropwise addition of dimethyl carbonate (5 mL, 5.35 g, 59 mmol). The resultant reaction mixture was stirred at ambient temperature for 90 minutes, then poured into water (150 mL) and extracted with ether (3×50 mL) and EtOAc (50 mL). The combined organic extracts were dried over $MgSO_4$ and concentrated, in vacuo, to give an orange oil which was purified by flash chromatography. Elution with hexane:EtOAc (4:1) provided the product as a yellow oil (1.28 g, 68%)

The following analyses indicated that the product was methyl 7-oxo-4,5,6,7-tetrahydrobenzothiophene-6-carboxylate.

NMR ($CDCl_3$) δ=7.66 (1H, d, J=4.8 Hz), 6.97 (1H, d, J=4.8, Hz), 3.77 (3H, s), 3.61 (1H, dd, J=4.8, 9.0 Hz), 3.05 (1H, ddd, J=4.9, 6.5, 17.1 Hz), 2.87 (1H, ddd, J=4.9, 8.2, 17.1 Hz), 2.62–2.50 (1H, m), 2.43–2.33 (1H, m); Anal. ($C_{10}H_{10}O_3S$) C, H, S (g). methyl 7-hydroxy-4,5,6,7-tetrahydrobenzothiophene-6-carboxylate and 7-hydroxy-6-(hydroxymethyl)-4,5,6,7-tetrahydrobenzothiophene To a solution of methyl 7-oxo-4,5,6,7-tetrahydrobenzothio-phene-6-carboxylate 8(f) (2.57 g, 12.2 mmol) in THF (15 mL) and $CH_3OH$ (10 mL) at 0° was added, portionwise, $NaBH_4$ (465 mg, 12.2 mmol). The resultant reaction mixture was stirred for 2 hours, gradually warming to 15°, then poured into saturated $NH_4Cl$ (30 mL). The layers were separated and the aqueous phase extracted with EtOAc (30 mL). The combined organic extracts were dried over $MgSO_4$ and concentrated, in vacuo, to give a yellow oil which was purified by flash chromatography. Elution with hexane:EtOAc (3:2) provided two separate products. The faster-eluting product was a yellow oil (0.91 g, 35%).

The following analyses indicated that this product was methyl 7-hydroxy-4,5,6,7-tetrahydrobenzothiophene-6-carboxylate.

NMR ($CDCl_3$) δ=7.25 (1H, d, J=5.1 Hz), 6.78 (1H, d, J=5.1 Hz), 5.23–5.16 (1H, m), 3.78 (3H, s), 3.09 (1H, broad), 2.90–2.57 (3H, m), 2.38–2.05 (2H, m); Anal. ($C_{10}H_{12}O_3S$) C, H, S The slower-eluting product was a milky-white cum (1.28 g, 57%)

The following analyses indicated that this second product was 7-hydroxy-6-(hydroxymethyl)-4,5,6,7-tetrahydrobenzo-thiophene.

NMR ($CDCl_3$) δ=7.24 (1H, d, J=5.1 Hz), 6.79 (1H, d, J=5.1 Hz), 5.03–4.85 (1H, m), 3.96–3.79 (2H, m), 2.86–2.54 (3H, m), 2.07–1.94 (1H, m), 1.91–1.80 (1H, m), 1.77–1.71 (1H, m), 1.63–1.48 (1H, m); Anal. ($C_9H_{12}O_2S$) C, H, S (h). methyl 4,5,6,7-tetrahydrobenzothiophene-6-carboxylate To a solution of methyl 7-hydroxy-4,5,6,7-tetrahydrobenzo-thiophene-6-carboxylate 8(g) (459 mg, 2.2 mmol) and $Et_3SiH$ (0.7 mL, 510 mg, 4.4 mmol) in $CH_2Cl_2$ (10 mL), under argon at −5°, was added $BF_3$-$Et_2O$ (0.55 mL, 635 mg, 4.5 mmol). The resultant reaction mixture was stirred for 3 hours, gradually warming to 15°, then poured into saturated $NaHCO_3$(30 mL). After addition of $K_2CO_3$ (~1 g), the layers were separated and the aqueous phase was extracted with $CH_2Cl_2$ (10 mL) and ether (2×15 mL). The combined organic extracts were dried over $MgSO_4$ and concentrated, in vacuo, to give a yellow oil which was purified by flash chromatography. Elution with hexane:EtOAc (95:5) provided the product as a colourless oil (300 mg, 71%).

The following analyses indicated that the product was methyl 4,5,6,7-tetrahydrobenzothiophene-6-carboxylate.

NMR ($CDCl_3$) δ=7.07 (1H, d, J=5.1 Hz), 6.75 (1H, d, J=5.1 Hz), 3.73 (3H, s), 3.11–2.94 (2H, m), 2.85–2.59 (3H, m), 2.27–2.18 (1H, m), 1.94–1.81 (1H, m); Anal. ($C_{10}H_{12}O_2S$) C, H, S (i). 6-(hydroxymethyl)-4,5,6,7-tetrahydrobenzothiophene Method A:

A solution of methyl 4,5,6,7-tetrahydrobenzothiophene-6-carboxylate 8(h) (209 mg, 1.1 mmol) in THF (6 mL) was added to a slurry of LiAlH$_4$ (50 mg, 1.3 mmol) in THF (3 mL).

The resultant reaction mixture was heated at reflux for 3 hours. After cooling to room temperature, the crude reaction mixture was diluted with saturated NH$_4$Cl (20 mL). The layers were separated and the aqueous phase extracted with ether (10 mL), then with DtOAc (2×10 mL). The combined organic extracts were dried over MgSO$_4$ and concentrated, in vacuo, to provide the product as a colorless oil (167 mg, 93%).

Method B:

To a solution of 7-hydroxy-6-(hydroxymethyl)-4,5,6,7-tetrahydrobenzothiophene (988 mg, 5.4 mmol) and Et$_3$SiH (1.8 mL, 1.31 g, 11.3 mmol) in CH$_2$Cl$_2$ (25 mL), under argon at −520, was added BF$_3$-Et$_2$O (1.4 mL, 1.62 g, 11.3 mmol). The resultant reaction mixture was stirred for 3 hours, gradually warming to 10°, then poured into saturated NaHCO$_3$ (50 mL). After addition of K$_2$CO$_3$ (1.5 g), the layers were separated and the aqueous phase extracted with ether (2×40 mL). The combined organic extracts were dried over MgSO$_4$ and concentrated, in vacuo, to give a yellow oil which was purified by flash chromatography. Elution with hexane:EtOAc (2:1) provided the product as a colorless oil (593 mg, 66%).

The following analyses indicated that the product was 6-(hydroxymethyl)-5,5,6,7-tetrahydrobenzothiophene.

NMR (CDCl$_3$) δ=7.06 (1H, d, J=5.1 Hz), 6.76 (1H, d, J=5.1 Hz), 3.66 (2H, d, J=6.4 Hz), 2.94 (1H, dd, J=5.2, 16.2 Hz), 2.79–2.71 (1H, m), 2.68–2.46 (2H, m), 2.11–1.96 (2H, m), 1.54–1.46 (1H, m); Anal. (C$_9$H$_{12}$OS) C, H, S (j). 6-[(t.-butyldimethylsilyloxy)methyl]-4,5,6,7-tetrahydrobenzothiophene To a solution of t-butyldimethylsilyl chloride (4.38 g, 29.1 mmol) in CH$_2$Cl$_2$ (25 mL) was added Et$_3$N (4.1 mL, 2.98 g, 29.4 mmol) followed by a solution of 6-(hydroxymethyl)-4,5,6,7-tetrahydrobenzothiophene 8(i) (4.44 g, 26.4 mmol) in CH$_2$Cl$_2$ (50 mL) and 4-(dimethylamino) pyridine (100 mg). The resultant reaction mixture was stirred at ambient temperature for 18 hours, then poured into water (100 mL). The layers were separated and the organic phase was washed with 0.5 N HCl (100 mL) and brine (100 mL), then dried over MgSO$_4$ and concentrated, in vacuo, to give a yellow oil which was purified by flash chromatography. Elution with hexane:EtOAc (95:5) provided the product as a colorless oil (6.49 g, 86%).

The following analyses indicated that the product was 6-[(t-butyldimethylsilyloxy)methyl]-4,5,6,7-tetrahydrobenzothiophene.

NMR (CDCl$_3$) δ=7.05 (1H, d, J=5.1 Hz), 6.75 (1H, d, J=5.1 Hz), 3.60 (2H, d, J=6.2 Hz), 2.89 (1H, dd, J=5.2, 16.2 Hz), 2.76–2.68 (1H, m), 2.65–2.42 (2H, m), 2.03–1.92 (2H, m), 1.53–1.41 (1H, m), 0.91 (9H, s), 0.06 (6H, s); Anal. (C$_{15}$H$_{26}$OSSi) C, H, S (k). diethyl N-(6-[(t-butyldimethylsilyloxy) methyl]-4,5,6,7-tetrahydrobenzothieno-2-yl) glutamate To a solution of 6-[(t.-butyldimethylsilyloxy) methyl]-4,5,6,7-tetrahydrobenzothiophene 8(j) (7.69 g, 27.2 mmol) in THF (100 mL), under argon at −70°, was added 2.5 M n-butyllithium in hexane (12 mL, 30 mmol). The resultant reaction mixture was stirred for an additional 40 minutes at −70°, then at −10° for 45 minutes while dry CO$_2$ was bubbled through the solution. The crude reaction mixture was subsequently poured into saturated NH$_4$CL (300 mL).

The layers were separated and the aqueous phase was extracted with ether (2×150 mL). The combined organic extracts were dried over Na$_2$SO$_4$ and concentrated, in vacuo, to give a yellow solid (8.24 g). This intermediate was employed in the subsequent reaction without any further purification.

To a solution of the aforementioned crude 6-[(t.-butyldimethylsilyloxy) methyl]-4,5,6,7-tetrahydrobenzothiophene-2-carboxylic acid (8.24 g), 1-hydroxybenzotriazole (4.05 g, 30 mmol) and glutamic acid diethyl ester hydrochloride (7.19 g, 30 mmol) in DMF (65 mL) were added diisopropyl-ethylamine (5.2 mL, 3.86 g, 30 mmol) and 1-(3-dimethylamino-propyl)-3-ethylcarbodiimide hydrochloride (5.75 g, 30 mmol). The resultant solution was stirred at ambient temperature for 16 hours, then poured into brine (400 mL), diluted with water (150 mL) and extracted with ether (3×250 mL). The combined organic extracts were dried over MgSO$_4$ and concentrated, in vacuc, to give a yellow oil which was purified by flash chromatography. Elution with hexane:EtOAc (4:1) provided the product as a yellow oil (6.63 g, 48%).

The following analyses indicated that the product was diethyl N-(6-[(t-butyldimethylsilyloxy) methyl]-4,5,6,7-tetra-hydrobenzothieno-2-yl) glutamate.

NMR (CDCl$_3$) δ=7.23 (1H, s), 6.67 (1H, d, J=7.7 Hz), 4.73 (1H, ddd, J=4.8, 7.7, 12.6 Hz), 4.22 (2H, q, J=7.1 Hz), 4.11 (2H, q, J=7.1 Hz), 3.59 (2H, d, J=6.2 Hz), 2.89 (1H, dd, J=5.1, 16.7 Hz), 2.75–2.23 (6H, m), 2.15–1.91 (3H, m), 1.56–1.42 (1H, m), 1.29 (3H, t, J=7.1 Hz), 1.23 (3H, t, J=7.1 Hz), 0.90 (9H, s), 0.06 (6H, s); Anal. (C$_{25}$H$_{41}$NO$_6$SSi) C, H, N, S (1). diethyl N-[6-(hydroxymethyl)-4,5,6,7-tetrahydrobenzothieno-2-yl] glutamate This material was prepared using the procedure described in example 5(b). From diethyl N-(6-[(t.-butyldimethylsilyloxy) methyl]-4,5,6,7-tetrahydrobenzothieno-2-yl) glutamate 8(k) (6.03 g, 11.8 mmol) there was obtained a yellow gum (3.62 g, 77%).

The following analyses indicated that the product was diethyl N-[6-(hydroxymethyl)-4,5,6,7-tetrahydrobenzothieno-2-yl] glutamate.

NMR (CDCl$_3$) δ=7.23 (1H, s), 6.70 (1H, d, J=7.6 Hz), 4.73 (1H, ddd, J=4.8, 7.6, 12.6 Hz), 4.22 (2H, q, J=7.1 Hz), 4.11 (2H, q, J=7.1 Hz), 3.66 (2H, d, J=6.3 Hz), 2.94 (1H, dd, J=5.0, 16.9 Hz), 2.77–2.22 (6H, m), 2.15–1.97 (3H, m), 1.57–1.44 (1H, m), 1.29 (3H, t, J=7.1 Hz), 1.23 (3H, t, J=7.1 Hz); Anal. (C$_{19}$H$_{27}$NO$_6$S.0.5H$_2$O) C, H, N, S (m). diethyl N-[6-(bromomethyl)-4,5,6,7-tetrahydrobenzothieno-2-yl] glutamate This material was prepared using the procedure described in example 2(d). From diethyl N-[6-(hydroxymethyl)-4,5,6,7-tetrahydrobenzothieno-2-yl] glutamate 8(1) (3.45 g, 8.7 mmol) there was obtained a colorless gum (3.68 g, 92%).

The following analyses indicated that the product was diethyl N-[6-(bromomethyl)-4,5,6,7-tetrahydrobenzothieno-2-yl] glutamate.

NMR (CDCl$_3$) δ=7.23 (1H, s), 6.73 (1H, d, J=7.6 Hz), 4.73 (1H, ddd, J=4.8, 7.6, 12.6 Hz), 4.23 (2H, q, J=7.2 Hz), 4.10 (2H, q, J=7.2 Hz), 3.49–3.41 (2H, m), 3.04 (1H, dd, J=5.0, 16.8 Hz), 2.79–2.03 (9H, m), 1.67–1.53 (1H, m), 1.29 (3H, t, J=7.2 Hz), 1.23 (3H, t, J=7.2 Hz); Anal. (C$_{19}$H$_{26}$NO$_5$SBr) C, H, N, S, Br (n). diethyl N-(6-[(acetylthio) methyl]-4,5.6.7-tetrahydrobenzothieno-2-yl)glutamate This material was prepared by using the procedure described in example 2(e). From diethyl N-[6-

(bromomethyl)-4,5,6,7-tetrahydrobenzothieno-2-yl] glutamate 8(m) (3.68 g, 8.0 mmol) there was obtained an orange oil (3.46 g, 95%).

The following analyses indicated that the product was diethyl N-(6-[(acetylthio) methyl]-4,5,6,7-tetrahydrobenzothieno-2-yl) glutamate.

NMR (CDCl$_3$) δ=7.21 (1H, s), 6.69 (1H, d, J=7.6 Hz), 4.72 (1H, ddd, J=4.8, 7.6, 12.6 Hz), 4.22 (2H, q, J=7.1 Hz), 4.11 (2H, q, J=7.1 Hz), 3.02–2.92 (3H, m), 2.74–2.38 (5H, m), 2.36 (3H, s), 2.35–2.22 (1H, m), 2.15=1.96 (3H, m), 1.57–1.46 (1H, m), 1.29 (3H, t, J=7.1 Hz), 1.23 (3H, t, J=7.1 Hz); Anal. (C$_{21}$H$_{29}$NO$_6$S$_2$.0.5H$_2$O) C, H, N, S (o). diethyl N-[6-(thiomethyl)-4,5,6,7-tetrahydrobenzothieno-2-yl] glutamate

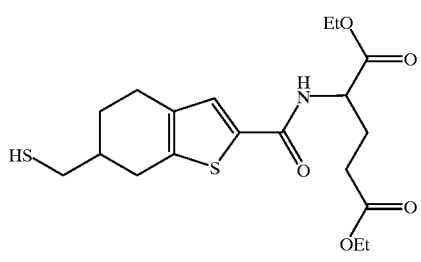

A solution of diethyl N-(6-[(acetylthio) methyl]-4,5,6,7-tetrahydrobenzothieno-2-yl) glutamate 8(n) (3.52 g, 7.7 mmol) in 0.5 N ethanolic HCl (60 mL) was heated at reflux for 3 hours. The reaction was diluted with water (25 mL) and the ethanol was removed by concentration, in vacuo. The aqueous residue was extracted with ether (2×50 mL). The combined organic extracts were dried over Na$_2$SO$_4$ and concentrated, in vacuo, to provide the product as an orange syrup (3.09 g, 97%).

The following analyses indicated that the product was diethyl N-[6-(thiomethyl)-4,5,6,7-tetrahydrobenzothieno-2-yl] glutamate.

NMR (CDCl$_3$) δ=7.23 (1H, s), 6.69 (1H, d, J=7.6 Hz), 4.73 (1H, ddd, J=4.8, 7.6, 12.6 Hz), 4.23 (2H, q, J=7.1 Hz), 4.12 (2H, q, J=7.1 Hz), 3.04 (1H, dd, J=5.0, 16.6 Hz), 2.77–2.23 (8H, m), 2.15–1.92 (3H, m), 1.59–1.48 (1H, m), 1.38 (1H, t, J=8.3 Hz), 1.30 (3H, t, J=7.1 Hz), 1.23 (3H, t, J=7.1 Hz); Anal. (C$_{19}$H$_{27}$NO$_5$S$_2$.0.25H$_2$O) C, H, N, S (p). diethyl N-(6-[([2,6-diamino-4(3H)-oxopyrimidin-5-yl] thio) methyl]-4,5,6,7-tetrahvdrobenzothieno-2-yl) glutamate This material was prepared using the procedure described in example 2(g). From diethyl N-[6-(thiomethyl)-4,5,6,7-tetra-hydrobenzothieno-2-yl] glutamate 8(o) (3.00 g, 7.3 mmol) and 5-bromo-2,6-diamino-4(3H)-pyrimidinone (1.44 g, 7.0 mmol) there was obtained a yellow solid (712 mg, 19%) melting at 122°–128°.

The following analyses indicated that the product was diethyl N-(6-[([2,6-diamino-4(3H)-oxopyrimidin-5-yl] thio) methyl]-4,5,6,7-tetrahydrobenzothieno-2-yl) glutamate.

NMR (DMSO-d6) δ=9.92 (1H, s), 8.53 (1H, d, J 7.5 Hz), 7.54 (1H, s), 6.28 (4H, br s), 4.34 (1H, ddd, J=5.3, 7.5, 9.4 Hz), 4.08 (2H, q, J=7.1 Hz), 4.03 (2H, q, J=7.1 Hz), 3.07 (1H, dd, J=4.4, 16.6 Hz), 2.66–2.43 (5H, m), 2.40 (2H, t, J=7.4 Hz), 2.09–1.89 (3H, m), 1.83–1.73 (1H, m), 1.48–1.37 (1H, m), 1.17 (3H, t, J=7.1 Hz), 1.15 (3H, t, J=7.1 Hz); Anal. (C$_{23}$H$_{31}$N$_5$O$_6$S$_2$) C, H, N, S (q). N-(6-[([2,6-diamino-4(3H)-oxopyrimidin-5-yl] thio) methyl]-4,5,6,7-tetrahydrobenzothieno-2-yl) glutamic acid

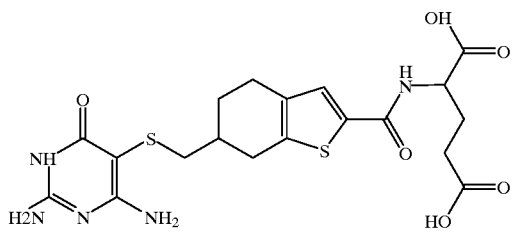

This material was prepared using the procedure described in example 2(j). From diethyl N-(6-[([2,6-diamino-4(3H)-oxopyrimidin-5-yl] thio) methyl]-4,5,6,7-tetrahydrobenzothieno-2-yl) glutamate 8(p) (594 mg, 1.1 mmol) there was obtained a white solid (493 mg, 93%) melting at 227°–230° (dec.).

The following analyses indicated that the product was N-(6-[([2,6-diamino-4(3H)-oxopyrimidin-5-yl] thio) methyl]-4,5,6,7-tetrahydrobenzothieno-2-yl) glutamic acid.

NMR (DMSO-d6) δ=12.38 (2H, broad), 10.08 (1H, broad), 8.42 (1H, d, J=7.8 Hz), 7.53 (1H, s), 6.44 (4H, br s), 4.30 (1H, ddd, J=4.6, 7.8, 12.6 Hz), 3.07 (1H, dd, J=4.3, 16.6 Hz), 2.66–2.36 (5H, m), 2.31 (2H, t, J=7.3 Hz), 2.10–1.77 (4H, m), 1.46–1.37 (1H, m); Anal. (C$_{19}$H$_{23}$N$_5$O$_6$S$_2$.0.7H$_2$O) C, H, N, S

EXAMPLE 9

Synthesis of N-(5-[2-([2,6-Diamino-4(3H)-oxopyrimidin-5-yl]thio)ethyl]thieno-2-yl)-L-glutamic acid This compound of formula X, wherein Ar is unsubstituted thienylene, A is sulfur and R$_1$, R$_2$ and R$_3$ are all hydrogen, was synthesized by the following process.

9a 2-[2-(t-Butyldimethylsilyloxy)ethyl]thiophene

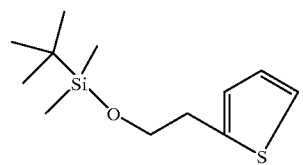

To a solution of t-butyldimethylsilyl chloride (26.38 g, 0.18 mol), triethylamine (25 mL, 0.18 mol) and 4-(dimethylamino)pyridine (300 mg, 2.5 mmol) in CH$_2$Cl$_2$ (200 mL) under an argon atmosphere at −5° C. was added, dropwise, 2-(2-thienyl)ethanol (18 mL, 0.16 mol). The resultant reaction mixture was stirred at 0° C. for 30 minutes, then at room temperature overnight. The crude reaction mixture was poured into water (300 mL), and the layers were separated. The organic phase was washed with 0.5N HCl (200 mL), then with brine (200 mL), dried over Na$_2$SO$_4$ and concentrated, in vacuo, to give a yellow oil, contaminated with a white solid, which was purified by flash chromatography. Elution with hexane/ethyl acetate (95.:5) yielded the product as a yellow oil (38.73 g, 99% yield).

NMR (CDCl$_3$) δ=7.13 (1H, d, J=5.1 Hz), 6.92 (1H, dd, J=3.3, 5.1 Hz), 6.83 (1H, d, J=3.3 Hz), 3.82 (2H, t, J=6.7 Hz), 3.03 (2H,t, J=6.7 Hz), 0.89 (9H, s), 0.03 (6H, s); Anal. (C$_{12}$H$_{22}$O SSi)C,H,S 9b) 5-[2(t-Butyldimethylsilyloxy)ethyl]thiophene-2-carboxylic acid and Methyl 5-(2-hydroxylethyl)thiophene-2-carboxylate

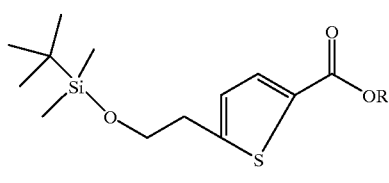

A 1.6M solution of n-butyllithium in hexane (140 mL, 0.22 mol) was added to a solution of 36.16 g (0.15 mol) of 9a in 350 mL of THF under argon at −75° C. The resultant reaction mixture was stirred for 1 hour at −70° C. Dry $CO_2$ was then bubbled through this solution for 40 minutes at −65° C., then for 60 minutes at −5° C. and finally for an additional 75 minutes while warming to room temperature. The crude reaction mixture was poured into a mixture of saturated $NH_4Cl$ (600 mL) and ice (600 g) and extracted with 300 mL of ether, then twice with 300 mL portions of ethyl acetate. The combined organic extracts were dried over $Na_2SO_4$ and concentrated, in vacuo, to give 47 g of a yellow solid which was used without further purification.

The above product (47 g) was dissolved in methanol (1 L) containing conc. $H_2SO_4$ (10 mL), and this solution was refluxed overnight. The solvent was removed by concentration, in vacuo, and the residue was partitioned between saturated $NaHCO_3$ (300 mL) and ether (300 mL). The layers were separated and the aqueous phase extracted twice with 300 mL of ethyl acetate. The combined organic extracts were dried over $Na_2SO_4$ and concentrated, in vacuo, yielding an orange oil which was purified by flash chromatography. Elution with 2:1 hexane/ethyl acetate provided the product as a yellow oil (12.31 g, 44% yield).

NMR ($CDCl_3$) δ=7.66 (1H, d, J=3.7 HZ), 6.88 (1H,d,J=3.7 Hz), 3.89 (2H,t,J=6.2 Hz), 3.86 (3H, s), 3.09 (2H, t, J=6.2 Hz); Anal. ($C_8H_{10}O_3S$) C, H, S 9c) Methyl 5-(2-bromoethyl)thiophene-2-carboxylate

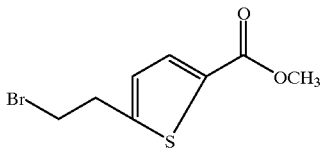

A solution of 11.2 g (42 mmol) of triphenylphosphine in 50 mL of methylene chloride was added dropwise to a solution of 6.52 g, (35 mmol) of 9b) and 13.93 g (42 mmol) of $CBr_4$ in 100 mL of methylene chloride at 0° C. The resultant reaction mixture was stirred for 60 minutes at 0°, then overnight at room temperature. The solvent was removed by concentration, in vacuo, and the residue obtained was purified by flash chromatography. Elution with hexane/ethylene acetate (9:1) yielded the product as a yellow oil (7.74 g, 89% yield).

NMR ($CDCl_3$) δ=7.66 (1H, d, J=3.8 Hz), 6.89 (1H, d, J=3.8 Hz), 3.87 (3H, s), 3.58 (2H, t, J=7.1 Hz), 3.38 (2H, t, J=7.1 Hz); Anal. ($C_8H_9O_2S$ Br) C, H, S, Br 9d) Methyl 5-[2-(acetylthio)ethyl]thiophene-2-carboxylate

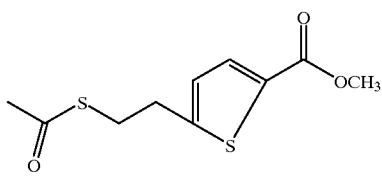

A mixture of 6.23 g (25 mmol) of 9c and 5.71 g (50 mmol) of potassium thiolacetate in 100 mL of acetone was heated at reflux for 30 minutes. After cooling to room temperature, the crude reaction mixture was filtered, and the filtrate was concentrated, in vacuo. The residue obtained was partitioned between ether and water (150 mL each). The layers were separated and the aqueous phase was extracted with 100 mL of ether and 100 mL of ethyl acetate. The combined organic extracts were dried over $Na_2SO_4$ and concentrated, in vacuo, yielding a red oil which was purified by flash chromatography. Elution with hexane/ethyl acetate (9:1) yielded the product as a yellow solid (5.61 g, 92% yield) mp 67°–68° C.

NMR ($CDCl_3$) δ=7.64 (1H, d, J=3.7 Hz), 6.85 (1H, d, J=3.7 Hz), 3.86 (3H, s), 3.19–3.06 (4H, m), 2.35 (3H, s); Anal. ($C_{10}H_{12}O_3S_2$) C, H, S 9e) Methyl 5-(2-thioethyl)thiophene-2-carboxylate

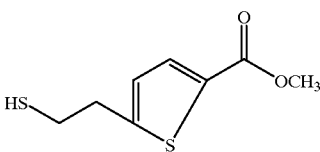

A solution of 4.89 g (20 mmol) of 9d in 1N methanolic HCl (75 mL) was heated at reflux for 2 hours. The reaction was diluted with water (50 mL) and the methanol was removed by concentration, in vacuo. The aqueous residue was extracted with ether (2×75 mL). The combined organic extracts were dried over $Na_2SO_4$ and concentrated, in vacuo, to provide the product as a yellow oil (3.93 g, 97% yield).

NMR ($CDCl_3$ δ=7.66 (1H, d, J=3.7 Hz), 6.86 (1H, d, J=3.7 Hz), 3.87 (3H, s), 3.14 (2H, t, J=7.1 Hz), 2.83 (2H, dt, J=8.2, 7.1 Hz), 1.50 (1H, t, J=8.2 Hz); Anal. ($C_8H_{10}O_2S_2$) C, H, S 9f) Methyl 5-(2-[(2,6-diamino-4(3H)-oxopyrimidin-5-yl)thio]ethyl)thiophene-2-carboxylate

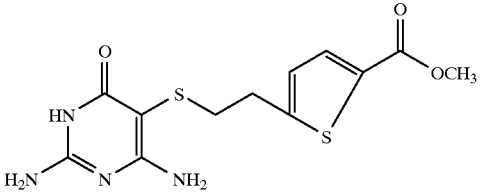

Argon was bubbled through a slurry of 3.00 g (14.6 mmol) of 5-bromo-2,6-diamino-4(3H)-pyrimidinone in 25 mL of DMF. To this slurry was added a solution of 3.24 g (16.0 mmol) of 9e in 30 mL of DXF and 5 mL (3.71 g, 28.7 mmol) of diisopropylethylamine. The resultant reaction mixture was heated at 100° C. for 90 minutes, then poured into water (350 mL). The precipitate that formed was collected by filtration, washed twice with 75 mL of water then twice with 75 mL of ether to provide the product as an off-white solid (3.22 g, 67% yield) mp 228°–229° C.

NMR (DMSO-d6) δ=9.98 (1H, s), 7.62 (1H, d, J=3.6 Hz), 7.02 (1H, d, J=3.6 HZ), 6.33 (4H, br s), 3.77 (3H, s), 2.98 (2H, t, J=7.1 Hz), 2.72 (2H, t, J=7.1 Hz); Anal. ($C_{12}H_{14}N_4O_3S_2$) C,H,N,S 9g) 5-(2-[(2,6-Diamino-4(3H)-oxopyrimidin-5-yl)thio]ethyl)thiophene-2-carboxylic acid

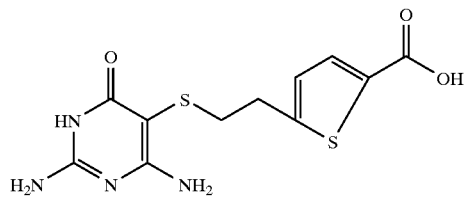

A suspension of 2.94 g (9.0 mmol) of 9f in 125 mL of 1N NaOH was stirred overnight at room temperature, then filtered. The filtrate was acidified to ~pH5 by addition of ~30 mL of 6N HCl. The precipitate that formed was collected by filtration and washed twice with 25 mL of water to provide the product as a yellow powder (2.65 g, 94% yield mp 273° (dec)).

NMR (DMSO-d6) δ=12.86 (1H, broad), 9.99 (1H, br s), 7.53 (1H, d, J=3.7 Hz), 6.97 (1H, d, J=3.7 Hz), 6.34 (4H, br s), 2.97 (2H, t, J=7.3 Hz), 2.72 (2H, t, J=7.3 Hz); Anal. ($C_{11}H_{12}N_4O_3S_2$) C,H,N,S 9h) Diethyl N-(5-[2-([2,6-diamino-4(3H)- oxopyrimidin-5-yl]thio)ethyl]thieno-2-yll-L-glutamate

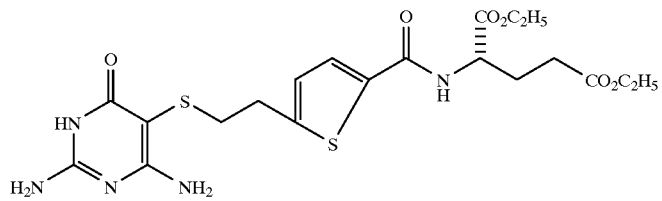

A solution of 1.87 g (6.0 mmol) of 9 g, 3.3 mL (3.04 g, 30 mmol) of 4-methylmorpholine and 2.41 g (9.0 mmol) of phenyl N-phenylphosphoramidochloridate in 75 mL of 1-methyl-2-pyrrolidinone was stirred for one hour prior to addition of 2.88 g (12.0 mmol) of L-glutamic acid diethyl ester hydrochloride. The resultant reaction mixture was stirred overnight at room temperature, then concentrated, in vacuo. The residue obtained was partitioned between chloroform and water (100 mL each). The layers were separated and the aqueous phase extracted with 100 mL of chloroform. The combined organic extracts were dried over $Na_2SO_4$ and concentrated, in vacuo, yielding an orange gum which was purified by flash chromatography. Elution with 4% methanol in chloroform yielded the product as a pale yellow solid (1.41 g, 47% yield, mp 95°–96° C.).

NMR (DMSO-d6) δ=9.98 (1H, s), 8.61 (1H, d, J=7.5 Hz), 7.67 (1H, d, J=3.0 Hz), 6.94 (1H, d, J=3.0 Hz), 6.32 (4H, br s), 4.40–4.33 (1H, m), 4.09 (2H, q, J=7.1 Hz), 4.03 (2H, q, J=7.1 Hz), 2.94 (2H, t, J=7.3 Hz), 2.70 (2H, t, J=7.3 Hz), 2.40 (2H, t, J=7.4 Hz), 2.13–2.01 (1H, m), 2.00–1.91 (1H, m), 1.17 (3H, t, J=7.1 Hz), 1.15 (3H, t, J 7.1 Hz); Anal. ($C_{20}H_{27}N_5O_6S_2$: 0.5 $H_2O$) C,H,N,S 9i) N-(5-[2-([2,6-Diamino-4(3H)-oxopyrimidin-5-yl]thio)ethyl]thieno-2-yl)-L-glutamic acid

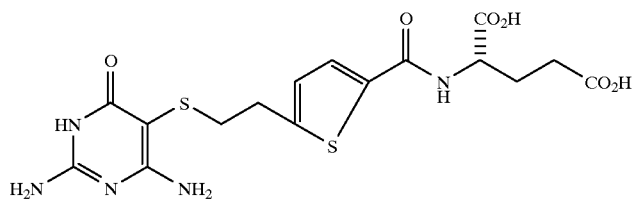

A solution of 1.16 g (2.3 mmol) of 9h 90 mL of 1N NaOH was stirred at room temperature for 70 hours, then acidified to ~pH5 by addition of ~20 mL of 6N HCl. The precipitate that formed was collected by filtration and washed three times with 10 mL of water to yield the product as an off-white powder (878 mg, 85% yield, mp 228–230° C. (dec)).

NMR (DMSO-d6) δ=12.41 (2H, broad), 10.02 (1H, br s), 8.51 (1H, d, J=7.7 Hz), 7.67 (1H, d, J=3.3 Hz), 6.94 (1H, d, J=3.3 Hz), 6.36 (4H, br s), 4.36–4.28 (1H, m), 2.94 (2H, t, J=7.3 Hz), 2.70 (2H, t, J=7.3 Hz), 2.32 (2H, t, J=7.1 Hz), 2.12–2.00 (1H, m), 1.95–1.85 (1H, m); Anal ($C_{16}H_{19}N_5O_6S_2$) C,H,N,S.

EXAMPLE 10

Synthesis of N-(4[4-[2-([2,6-Diamino-4(3H)-oxopyrimidin-5-yl]thio)ethyl]benzoyl)-L-glutamic acid This compound of formula X, wherein A is sulfur, Ar is unsubstituted phenylene and $R_1$, $R_2$ and $R_3$ are all hydrogen, was synthesized by the following process.

10a) Methyl 4-(2-bromoethyl benzoate

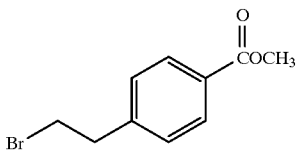

A solution of 9.16 g (40 mmol) of 4-(2-bromoethyl)-benzoic acid in 100 mL of THF was combined with an ether solution containing excess diazomethane. The excess diazomethane was consumed by addition of glacial acetic acid and the resultant solution was concentrated, in vacuo. The residue obtained was partitioned between saturated NaHCO₃ (150 mL) and ethyl acetate (150 ml). The layers were separated and the aqueous phase was extracted with ethyl acetate (70 mL). The combined organic extracts were dried over Na₂SO₄ and concentrated in vacuo, yielding the product as a yellow oil (9.65 g, 99% yield).

NMR (CDCl₃) δ=8.01 (2H, d, J=8.3 Hz), 7.30 (2H, d, J=8.3 Hz), 3.92 (3H, s), 3.59 (2H, t, J=7.4 Hz), 3.23 (2H, t, J=7.4 Hz); Anal. (C₁₀H₁₁O₂Br) C, H, Br 10b) Methyl 4-[2-(acetylthio)ethyl]benzoate

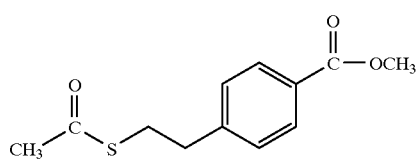

Methyl 4-[2-(acetylthio)ethyl]benzoate was prepared by following the procedure described for 9d. Thus from 1.22 g (5.0 mmol) of 10a 1.14 g of 10b was obtained (96% yield) as a yellow solid (mp 68° C.).

NMR (CDCl₃) δ=7.97 (2H, d, J=8.2 Hz), 7.29 (2H, d, J=8.2 Hz), 3.91 (3H, s), 3.13 (2H, t, J=7.3 Hz), 2.92 (2H, t, J=7.3 Hz), 2.33 (3H, s); Anal. (C₁₂H₁₄O₃S) C, H, S 10c) Methyl 4-(2-thioethyl)benzoate

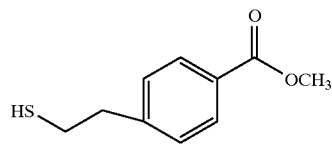

Methyl 4-(2-thioethyl)benzoate was prepared by following the procedure described for 9e. Thus from 1.05 g (4.4 mmol) of 10b there was obtained 8.53 mg of 10c as a yellow oil (99% yield).

NMR (CDCl₃) δ=7.98 (2H, d, J=8.2 Hz), 7.27 (2H, d, J=8.2 Hz), 3.91 (3H, s), 2.98 (2H, t, J=7.3 Hz), 2.81 (2H, dt, J=7.9, 7.3 Hz), 1.37 (1H, t, J=7.9 Hz); Anal. (C₁₀H₁₂O₂S) C, H, S 10d) Methyl 4-(2-[(2,6-diamino-4(3H)-oxopyrimidin-5-yl)thio]ethyl)benzoate

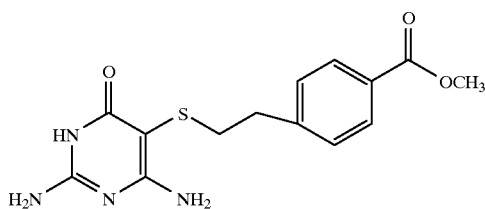

Methyl 4-(2-[(2,6-diamino-4(3H)-oxopyrimidin-5-yl)thio]ethyl)benzoate was prepared by following the procedure described for 9f. Thus, from 2.45 g (12.5 mmol) of 10c there was obtained 1.58 g of 10d as a white solid (43% yield, mp 286°–288° C. (dec)).

NMR (DMSO-d6) δ9.98 (1H, br s), 7.85 (2H, d, J=8.2 Hz), 7.36 (2H, d, J=8.2 Hz), 6.33 (4H, broad), 3.82 (3H, s), 2.81 (2H, t, J=7.3 Hz), 2.70 (2H, t, J=7.3 Hz); Anal. (C₁₄H₁₆N₄O₃S) C, H, N, S 10e) 4-(2-[(2,6-Diamino-4(3H)-oxopryrimidin-5-yl)thio]ethyl)benzoic acid

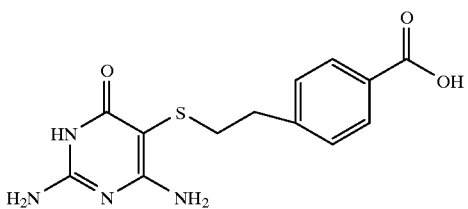

4-(2-[(2,6-Diamino-4(3H)-oxopyrimidin-5-yl)thio]ethyl)benzoic acid was prepared by following the procedure described for 9g. Thus from 1.44 g (4.5 mmol) of 10d, there was obtained 1.27 g of 10e as a white solid (93% yield, mp 291°–292°).

NMR (DMSO-d6) δ=12.78 (1H, br s), 9.98 (1H, br s), 7.82 (2H, d, J=8.2 Hz), 7.32 (2H, d, J=8.2 Hz), 6.31 (4H, broad), 2.80 (2H, t, J=7.3 Hz), 2.69 (2H, t, J=7.3 Hz); Anal. (C₁₃H₁₄N₄O₃S : 0.5 H₂O) C, H, N, S 10f) Diethyl N-(4-[2-([2.6-diamino-4(3H)-oxopyrimidin-5-yl]thio)ethyl]benzoyl)-L-glutamate

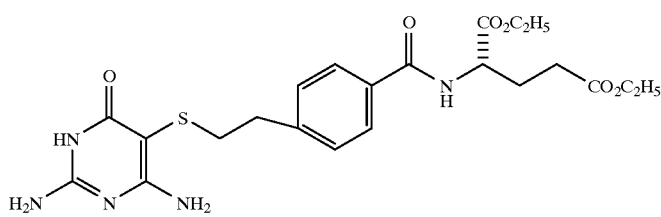

Diethyl N-(4-[2-([2,6-diamino-4(3H)-oxopyrimidin-5-yl]thio)ethyl]benzoyl)-L-glutamate was prepared by following the procedure described for 9h. Thus, from 919 mg (3.0 mmol) of 10e, there was obtained 660 mg of 10f as a white solid (45% yield, mp 105°–107° C.).

NMR (acetone-d6) δ=10.72 (1H, s), 7.87 (1H, d, J=8.0 Hz), 7.80 (2H, d, J=7.8 Hz), 7.31 (2H, d, J=7.8 Hz), 6.62 (2H, s), 6.11 (2H, s), 4.65 (1H, ddd, J=5.3, 8.0, 13.3 Hz), 4.15 (2H, q, J=7.1 Hz), 4.07 (2H, q, J 7.1 Hz), 2.93–2.78 (4H, m), 2.50 (2H, t, J=7.3 Hz), 2.29–2.17 (1H, m), 2.15–2.05 (1H, m), 1.23 (3H, t, J=7.1 Hz), 1.18 (3H, t, J=7.1 Hz); Anal. ($C_{22}H_{29}N_5O_6S$) C, H, N, S 10g N-(4-[2-([2,6-diamino-4(3H)-oxopyrimidin-5-yl]thio)ethyl]benzoyl-L-glutamic acid

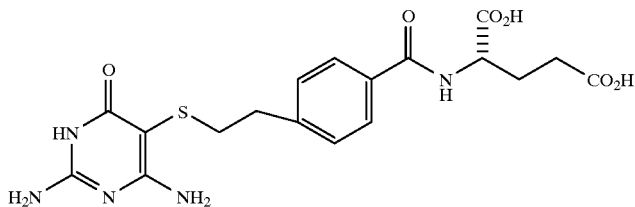

N-(4-[2-([2,6-Diamino-4(3H)-oxopyrimidin-5-yl]thio)ethyl]benzoyl)-L-glutamic acid was prepared by following the procedure described for 9i. Thus from 246 mg (0.5 mmol) of 10f there was obtained 76 mg of 10g (35% yield, mp 177–181° C.

NMR (DMSO-d6) δ=10.01 (1H, br s), 8.49 (1H, d, J=7.6 Hz), 7.77 (2H, d, J=8.1 Hz), 7.30 (2H, d, J=8.1 Hz), 6.33 (4H, broad), 4.35 (1H, ddd, J=5.3, 7.6, 13.0 Hz), 2.78 (2H, t, J=6.8 Hz), 2.69 (2H, t, J=6.8 Hz), 2.33 (2H, t, J=7.3 Hz), 2.09–1.89 (2H, m); Anal. ($C_{18}H_{21}N_5O_6S \cdot 1.05 H_2O$) C, H, N, S

EXAMPLE 11

Biological and Biochemical Evaluation
In Vitro Testing

Cellular growth in the presence of the compounds according to the present invention was assessed using two cell lines: the L1210 murine leukemia (ATCC CCL 219) and CCRF-CEM, a human lymphoblastic leukemia line of T-cell origin (ATCC CCL 119). Both lines were maintained in RPMI 1640 medium containing 5% heat-inactivated fetal bovine serum without antibiotics.

$IC_{50}$ values were determined in 160 microliter microcultures each containing 1500 (L1210) or 10,000 (CCRF-CEM) cells established in 96 well plates in growth medium supplemented with 50 IU/mL penicillin and 50 mcg/mL streptomycin. Growth was measured over 3 days (L1210) or 5 days (CCRF-CEM) of continuous exposure to varying concentrations of each test compound added 4 hours after initial cell plating by the MITT-tetrazolium reduction assay of Mosmann T. J. (Immunol. meth. 65, 55–63 (1983)), modified according to Alley et al. (Cancer Res. 48, 589–601 (1988)). Water insoluble derivatives were dissolved in DMSO and diluted to a final concentration of 0.5% solvent in cell cultures.

Determination of Inhibition Constants for GARFT

Method I (used for examples 2–5 and 10):

GARFT inhibition constants were measured by the method of Cleland (Biochim. Biophys. Acta 67, 173–187 (1963)). Assays were done at 22° C. and initiated by addition of enzyme using the spectrophotometric assay of Young et al. (Biochemistry 23, 3979–3986 (1984)) and monitoring the reaction at 295 nm. The GARFT-domain of the human enzyme was used. The variable substrate was 10-formyl-5,8-dideazafolate at concentrations of 0.83 μM, 1.25 μM, 2.5 μM and 5 μM while the other substrate, GAR (glycinamide ribonucleotide), was held constant at 20 μM. The assay mix contained 20 mM Hepes pH 7.5, 20 μM GAR, and variable amounts of 10-formyl-5, 8-dideazafolate and inhibitor. For each inhibitor five concentrations were used ranging from 0 to approximately 3 Ki. The data were plotted as the velocity of the reaction versus the reciprocal of the 10-formyl-5, 8-dideaza-folate concentration. The inhibition constants were measured from a replot of the slopes of these lines obtained for each concentration of inhibitor versus the inhibitor concentration.

Method II (used for examples 6, 7, 8 and 9):

The GARFT assay method of Young, et al. (Biochemistry 23, 3979–3986(1984)) was modified and used as described below. Reaction mixtures contained the catalytic domain of the human GARFT, inhibitor, 20 μM glycinamide ribonucleotide (GAR), 10 or 20 μM $N^{10}$-formyl-5,8-dideazafolate (FDDF), and 50 mM Tris-Cl at pH 7.5. The reaction was initiated with the addition of enzyme to a final concentration of 11 nM and followed by monitoring the increase in absorbance at 294 nM at 20° C. ($\xi_{294}$=18.9 $mM^{-1}$ $cm^{-1}$).

GARFT constants ($K_i$) were determined from the dependence of the steady-state catalytic rate upon inhibitor and substrate concentration. The type of inhibition observed was determined to be competitive with respect to FDDF by the dependence of the apparent $K_i(K_{i,app})$ on the concentration of FDDF and was shown to be described by $K_{i,app}=K_i+(K_i/K_m)[FDDF]$. The michaelis constant $K_m$, was determined independently by the dependence of the catalytic rate upon FDDF concentration. Data for both the $K_m$ and $K_i$ determinations were fitted by non-linear methods to the Michaelis equation or the Michaelis equation for competitive inhibition as appropriate. Data resulting from the tight-binding inhibition was analyzed, and the $K_i$ was determined by fitting the data to the tight-binding equation of Morrison Biochem Biophys Acta 185, 269–286 (1969)) by non-linear methods.

| GARFT Inhibition and Cell Culture Data | | | |
|---|---|---|---|
| | GARFT | Cell Line, $IC_{50}$ (μM) | |
| Ex. | $K_i$ μM | L1210 | L1210-C192 | CCRF-CEM |
| 2 | 0.11 | 0.079 | 5.0 | 0.065 |
| 4 | 0.11 | 0.11 | 10.0 | 0.13 |
| 3 | 0.035 | 0.04 | 10.5 | 0.049 |
| 5 | 0.088 | 0.09 | 4.2 | 0.08 |
| 6 | 0.008 | 0.12 | >25 | 0.068 |
| 7 | 0.032 | 0.089 | 28 | 0.099 |
| 8 | 0.030 | 0.01 | 9.0 | 0.008 |
| 9 | 2.00 | 0.25 | 22 | 0.62 |
| 10 | 30 | 1.5 | 12 | 1.2 |

Determination of Inhibition Constants for AICARFT

The assay method of Black et al. (Anal Biochem 90, 397–401 (1978)) was modified and used as described below.

Buffers were degassed under vacuum prior to the preparation of substrate solutions and degassed buffer was used in the reaction mixtures. Reaction mixtures contained partially purified AICARFT from cultured CEM cells, inhibitor, 100 μM AICAR (5-aminoimidazole-4-carboxamide-ribonucleotide), 50 μM of a racemic mixture of $N_{10}$-formyl-tetrahydrofolate (FTHF), 25 mM KCl, 50 mM 2-mercaptoethanol and 50 mM Tris-Cl pH 7.4. The reaction was initiated with the addition of the enzyme solution to a final concentration of 0.1 mg/mL and the reaction followed by monitoring the increase in absorbance at 298 nm at 37° C. ($\xi_{298}$=28 $mM^{-1}$ $cm^{-1}$).

AICARFT inhibition constants ($K_i$) were determined from the dependence of the steady-state catalytic rate upon inhibitor and substrate concentration. The type of inhibition observed and the determination of $K_i$ was performed as described above for inhibitors of GARFT with the appropriate substrates and the AICARFT assay. Treatment of experimental data was essentially the same.

AICARFT Ki values for examples 9 and 10 were determined to be 35 and 60 μM respectively.

It will be apparent to those skilled in the art that various modifications and variations can be made in the processes and products of the present invention. Thus, it is intended that the present invention cover modifications and variations of this invention which fall within the scope of the appended and equivalent claims.

Specifically, it is recognized that no specific example has been given of making the polymeric polyglutamate form of the compounds of the present invention. One skilled in the art, however, could do this synthetically in accord with the literature methods. Normally, moreover, as explained above, polyglutamation, preferably with the addition of one to five glutamate units to the compounds of the present invention, more preferably, one to four glutamate units, will occur inside the cells.

We claim:

1. A compound having the formula I

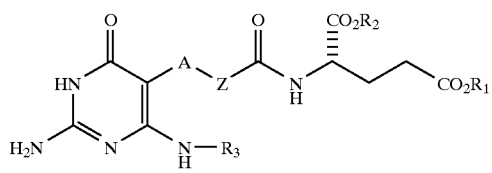

wherein:
A represents sulfur or selenium;
Z represents a combination of a substituted or unsubstituted non-cyclic spacer which separates A from the carbonyl carbon of the amido group by 1 to 10 atoms, said atoms being independently selected from carbon, oxygen, sulfur, nitrogen and phosphorous and at least one carbocyclic radical, said radical being substituted or unsubstituted mono- or fused or nonfused polycarbocyclic, wherein when said non-cyclic spacer is bonded to A, said non-cyclic spacer separates A from one of said carbocyclic radicals by 1 to 10 atoms and further wherein when said non-cyclic spacer is bonded to —C(O)—, said non-cyclic spacer separates —C(O))— from one of said carbocyclic radicals by 1 to 10 atoms;

$R_1$ and $R_2$ represent, independently, H or $C_1$ to $C_6$ alkyl or other readily lyzable groups; and $R_3$ represents H or a straight, branched or cyclic $C_1$ to $C_6$ alkyl group optionally carrying one or more halogen, hydroxyl or amine groups; or a pharmaceutically acceptable salt thereof.

2. A compound according to claim 1 having the formula II

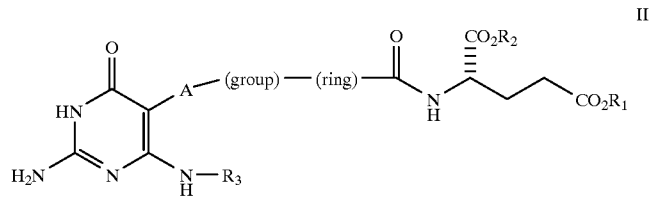

wherein:
A is sulfur or selenium;
Z is —(group)—(ring)—,
wherein (group) represents a non-cyclic spacer which separates A from (ring) by 1 to 5 atoms, said atoms being independently selected from carbon, oxygen, sulfur, nitrogen and phosphorous and optionally carrying one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$) alkyl groups, $C_2$ to $C_6$ alkynyl groups, acyl groups, halogen, amino groups, hydroxyl groups, nitro groups or mercapto groups, monocyclic carbo- or heterocyclic rings, and fused or non-fused poly-carbocyclic or poly-heterocyclic rings;

and wherein (ring) represents one or more of a substituted or unsubstituted monocyclic carbocylic ring or a fused or non-fused polycarbocyclic ring optionally substituted with one or more substituents selected from those recited for (group);

$R_1$ and $R_2$ represent, independently, H, $C_1$ to $C_6$ alkyl or other readily lyzable groups; and $R_3$ represents hydrogen or a straight, branched or cyclic $C_1$ to $C_6$ alkyl group optionally carrying halogen, hydroxyl or amine substitution; or a pharmaceutically acceptable salt thereof.

3. A compound according to claim 1 wherein the moiety Z is represented by Q—X—Ar wherein:

Q represents a $C_1$–$C_5$ alkylene, or a $C_2$–$C_5$ alkenylene or alkynylene radical optionally carrying one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$)alkyl groups, $C_2$ to $C_6$ alkynyl groups, acyl groups, halogen, amino groups, hydroxyl groups, nitro groups or mercapto groups, monocyclic carbo- or heterocyclic rings, and fused or non-fused poly-carbocyclic or poly-heterocyclic rings;

X represents a methylene, sulfur, oxygen or amino radical, optionally carrying one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$)alkyl groups, $C_2$ to $C_6$ alkynyl groups, acyl groups, halogen, amino groups, hydroxyl groups, nitro groups or mercapto groups, monocyclic carbo- or heterocyclic rings, and fused or non-fused poly-carbocyclic or poly-heterocyclic rings; and Ar represents a monocyclic carbocyclic aromatic ring or a bicyclic carbocyclic ring, all or a portion of which may be aromatic, and wherein the Ar may be fused to the monocyclic carbo- or heterocyclic ring of X, and wherein the Ar optionally carries one or more substituents independently selected from $C_1$ to $C_6$ alkyl or $C_2$ to $C_6$ alkenyl groups, $C_1$ to $C_6$ alkoxy or $C_1$ to $C_6$ alkoxy($C_1$ to $C_6$)alkyl groups, $C_2$ to $C_6$ alkynyl groups, acyl groups, halogen, amino groups, hydroxyl groups, nitro groups or mercapto groups, monocycliccarbo- or heterocyclic rings, and fused or non-fused poly-carbocyclic or poly-heterocyclic rings;

or a pharmaceutically acceptable salt thereof.

4. A compound or salt according to claim 2, wherein the moiety (group) represents a $C_1$ to $C_4$ alkylene group; and the moiety (ring) represents a substituted or unsubstituted, fused or non-fused carbocyclic ring system, or a substituted or unsubstituted, carbocyclic monocyclic ring system, or at least two monocyclic ring systems linked by a single bond, said monocyclic ring systems being independently substituted or unsubstituted.

5. A compound having the formula III

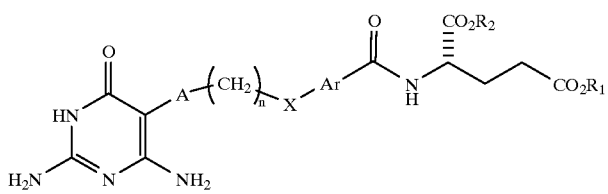

wherein:
n represents an integer from 0 to 5;
A represents sulfur or selenium;
X is methylene, monocyclic carbocyclic ring, O, S, or —NH—;
Ar is an aromatic carbocyclic radical, wherein Ar can form a fused bicyclic ring system with said ring of X; and
$R_1$ and $R_2$, which can be the same or different, are hydrogen or alkyl radicals having 1 to 6 carbon atoms; or a pharmaceutically acceptable salt thereof.

6. A compound or salt according to claim 5 wherein n is 2, A is sulfur, X is methylene, Ar is phenylene and $R_1$ and $R_2$ are hydrogen.

7. A compound or salt according to claim 5 wherein n is 2, A is sulfur, X is S, Ar is phenylene and $R_1$ and $R_2$ are hydrogen.

8. A compound or salt according to claim 5 wherein n is 2, A is sulfur, X is —NH—, Ar is phenylene and $R_1$ and $R_2$ are hydrogen.

9. A compound or salt according to claim 5 wherein n is 2, A is sulfur, X is methylene, Ar is phenylene and $R_1$ and $R_2$ are alkyl radicals having 1 to 6 carbon atoms.

10. A compound or salt according to claim 5 wherein n is 2, A is sulfur, X is sulfur, Ar is phenylene and $R_1$ and $R_2$ are ethyl groups.

11. A compound or salt according to claim 5, wherein n is 2, A is sulfur, X is —NH—, Ar is phenylene and $R_1$ and $R_2$ are ethyl groups.

12. An antiproliferative composition comprising a compound having the formula III

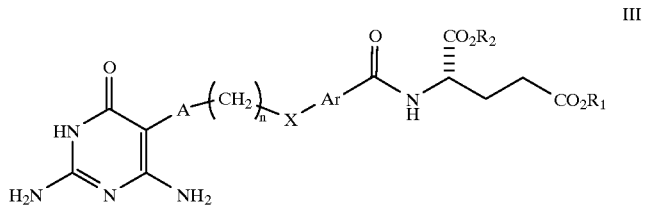

wherein n represents an integer from 0 to 5;

A is sulfur or selenium;

X is methylene, monocyclic carbocyclic ring, O, S, or —NH—;

Ar is an aromatic carbocyclic radical, wherein Ar can form a fused bicyclic ring system with said ring of X; and $R_1$ and $R_2$, which can be the same or different, are hydrogen or alkyl radicals having 1 to 6 carbon atoms; or a pharmaceutically acceptable salt thereof in combination with a pharmaceutically acceptable carrier.

13. A composition according to claim 12 wherein n is 2, A is sulfur, X is methylene, and Ar is phenylene.

14. A composition according to claim 12 wherein n is 2, A is sulfur, X is S, and Ar is phenylene.

15. A composition according to claim 12 wherein n is 2, A is sulfur, X is —NH—, and Ar is phenylene.

16. An antiproliferative composition comprising a compound having the formula I:

$$\text{[Formula I: pyrimidine-A-Z-C(O)NH-CH(CO}_2\text{R}_2\text{)-CH}_2\text{CH}_2\text{-CO}_2\text{R}_1\text{]}$$

wherein:

A represents sulfur or selenium;

Z represents a combination of a substituted or unsubstituted noncyclic spacer which separates A from the carbonyl carbon of the amido group by 1 to 10 atoms, said atoms being independently selected from carbon, oxygen, sulfur, nitrogen and phosphorus and at least one carbocyclic radical, said radical being substituted or unsubstituted mono- or fused or nonfused. polycarbocyclic, wherein when said non-cyclic spacer is bonded to A, said non-cyclic spacer separates A from one of said carbocyclic radicals by 1 to 10 atoms and further wherein when said non-cyclic spacer is bonded to —C(O)—, said noncyclic spacer separates —C(O)— from one of said carbocyclic radicals by 1 to 10 atoms;

$R_1$ and $R_2$ represent, independently, H, $C_1$ to $C_6$ alkyl or other readily lyzable groups; and $R_3$ represents H or a straight, branched or cyclic $C_1$ to $C_6$ alkyl group optionally carrying one or more halogen, hydroxyl or amine groups; or a pharmaceutically acceptable salt thereof; in combination with a pharmaceutically acceptable carrier.

17. A process for inhibiting the growth and proliferation of the cells of microorganisms and of higher organisms, which process comprises administering to a host in need of such treatment an effective amount of a compound having the structural formula I $$\text{[Formula I]}$$

wherein:

A represents sulfur or selenium;

Z represents a combination of a substituted or unsubstituted non-cyclic spacer which separates A from the carbonyl carbon of the amido group by 1 to 10 atoms, said atoms being independently selected from carbon, oxygen, sulfur, nitrogen and phosphorous and at least one carbocyclic radical, said radical being substituted or unsubstituted mono- or fused or non fused polycarbocyclic, wherein when said non-cyclic spacer is bonded to A, said non-cyclic spacer separates A from one of said carbocyclic radicals by 1 to 10 atoms and further wherein when said non-cyclic spacer is bonded to —C(O)—, said non-cyclic spacer separates —C(O)— from one of said carbocyclic radicals by 1 to 10 atoms;

$R_1$ and $R_2$ represent, independently, H, $C_1$ to $C_6$ alkyl or other readily lyzable groups; and $R_3$ represents H or straight, branched or cyclic $C_1$ to $C_6$ alkyl group optionally carrying one or more halogen, hydroxyl or amine groups; or a pharmaceutically acceptable salt thereof.

18. A process for inhibiting the growth and proliferation of the cells of microorganisms and higher organisms, which process comprises administering to a host in need of such treatment an effective amount of a compound having the structural formula III $$\text{[Formula III]}$$

wherein:

n represents an integer from 0 to 5;

A represents sulfur or selenium;

X is methylene, monocyclic carbocyclic ring, O, S, or —NH—;

Ar is an aromatic carbocyclic radical, wherein Ar can form a fused bicyclic ring system with said ring of X; and $R_1$ and $R_2$, which can be the same or different, are hydrogen or alkyl radicals having 1 to 6 carbon atoms; or a pharmaceutically acceptable salt thereof.

19. A process according to claim 18 wherein n is 2, A is sulfur, X is methylene and Ar is phenylene.

20. A process according to claim 18 wherein n is 2, A is sulfur, X is sulfur and Ar is phenylene.

21. A process according to claim 18 wherein n is 2, A is sulfur, X is —NH—, and Ar is phenylene.

22. A process for inhibiting GARFT comprising the step of administering to a host in need of such inhibition an effective amount of a compound having the formula I:

$$\text{[Formula I]}$$

wherein:

A represents sulfur or selenium;

Z represents a combination of a substituted or unsubstituted noncyclic spacer which separates A from the carbonyl carbon of the amido group by 1 to 10 atoms, said atoms being independently selected from carbon, oxygen, sulfur, nitrogen and phosphorus and at least one carbocyclic radical, said radical being substituted or unsubstituted mono- or fused or nonfused polycarboylic, wherein when said non-cyclic spacer is bonded to A, said non-cyclic spacer separates A from one of said carbocyclic radicals by 1 to 10 atoms and further wherein when said non-cyclic spacer is bonded to —C(O)—, said noncyclic spacer separates —C(O)— from one of said carbocyclic radicals by 1 to 10 atoms;

$R_1$ and $R_2$ represent, independently, H or $C_1$ to $C_6$ alkyl or other readily lyzable groups; and $R_3$ represents H or a straight, branched or cyclic $C_1$ to $C_6$ alkyl group optionally carrying one or more halogen, hydroxyl or amine groups; or a pharmaceutically acceptable salt thereof.

23. A compound of the formula X

X wherein:
A represents sulfur or selenium;
Ar represents an unsubstituted phenylene radical;
$R_1$ and $R_2$ represent, individually, hydrogen or $C_1$ to $C_6$ alkyl or other readily lyzable groups;
$R_3$ represents hydrogen or a straight, branched or cyclic $C_1$-$C_6$ alkyl group, optionally carrying one or more halogen, hydroxyl or amine groups; or
a pharmaceutically acceptable salt thereof.

24. A compound according to claim 23 wherein A is sulfur and Ar represents an unsubstituted phenylene radical.

25. A compound according to claim 23 wherein A is sulfur, Ar is unsubstituted phenylene; and $R_1$, $R_2$ and $R_3$ are hydrogen.

26. A method for inhibiting the growth and proliferation of the cells of microorganisms and higher organisms, which comprises administering to a host in need of such treatment an effective amount of the compound having the structural formula X as defined in claim 23, or a pharmaceutically acceptable salt thereof.

27. A method according to claim 26 wherein A is sulfur and Ar represents an unsubstituted phenylene radical.

28. A method according to claim 26 wherein A is sulfur, Ar is an unsubstituted phenylene radical; and $R_1$, $R_2$ and $R_3$ are hydrogen.

29. An antiproliferative composition comprising the compound having the formula X as defined in claim 23 or a pharmaceutically acceptable salt thereof, in combination with a pharmaceutically acceptable carrier.

30. A composition according to claim 29 wherein A is sulfur and Ar represents an unsubstituted phenylene radical.

31. A composition according to claim 29 wherein A is sulfur, Ar is an unsubstituted phenylene; and $R_1$, $R_2$ and $R_3$ are hydrogen.

32. A compound having the formula V

V wherein:
A represents sulfur or selenium;

Z represents a combination of a substituted or unsubstituted non-cyclic spacer which separates A from the carbonyl carbon of the C(O)—$R_4$ group by 1 to 10 atoms, said atoms being independently selected from carbon, oxygen, sulfur, nitrogen and phosphorous and at least one carbocyclic radical, said radical being substituted or unsubstituted mono- or fused or non-fused polycarbocylic, wherein said non-cyclic spacer separates A from one of said carbocyclic radicals by 1 to 10 atoms;

$R_3$ represents H or a straight, branched or cyclic ($C_1$ to $C_6$) alkyl group, optionally carrying one or more hydroxyl or amine groups; and $R_4$ represents hydroxy, a ($C_1$ to $C_6$) alkyloxy group optionally carrying one or more hydroxyl or amine groups, or a protected or unprotected amino acid linked to the acyl group of formula V by the amine portion of the amino acid;

or a pharmaceutically acceptable salt thereof.

33. A process for inhibiting AICARFT comprising the step of administering to a host in need of such inhibition an effective amount of a compound having the formula X:

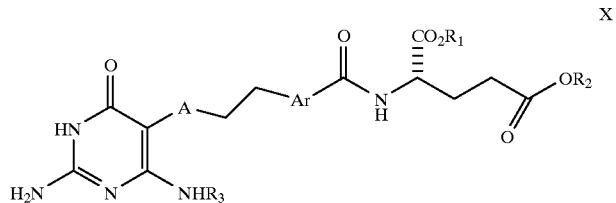

wherein:
  A represents sulfur or selenium;
  Ar represents an unsubstituted phenylene radical;
  $R_1$ and $R_2$ represent, individually, hydrogen or $C_1$ to $C_6$ alkyl or other readily lyzable groups;
  $R_3$ represents hydrogen or a straight, branched or cyclic $C_1$–$C_6$ alkyl group, optionally carrying one or more halogen, hydroxyl or amine groups; or
  a pharmaceutically acceptable salt thereof.

* * * * *